US00RE37710E

(19) United States
(12) Reissued Patent
McBride et al.

(10) Patent Number: US RE37,710 E
(45) Date of Reissued Patent: May 21, 2002

(54) RADIOMETAL-BINDING ANALOGUES OF LUTEINIZING HORMONE RELEASING HORMONE

(75) Inventors: William J. McBride, Summit; Habibe Karacay, Matawan; Gary L. Griffiths, Morristown, all of NJ (US)

(73) Assignee: Immunomedics, Inc., Morris Plains, NJ (US)

(21) Appl. No.: 09/572,339

(22) Filed: May 18, 2000

Related U.S. Patent Documents

Reissue of:
(64) Patent No.: 5,753,206
Issued: May 19, 1998
Appl. No.: 08/474,555
Filed: Jun. 7, 1995

(51) Int. Cl.[7] ..... A61K 51/00; A61M 36/14
(52) U.S. Cl. ..... 424/1.69; 424/1.11; 424/1.65; 424/9.1; 530/300; 530/328; 530/313; 534/10; 534/14
(58) Field of Search ..... 424/1.11, 1.65, 424/1.69, 9.1; 534/7, 10–16; 530/300, 313, 324, 325, 326, 327, 328, 329, 330, 333

(56) References Cited

U.S. PATENT DOCUMENTS

| | | | | |
|---|---|---|---|---|
| 4,444,690 A | | 4/1984 | Fritzberg | 260/429 J |
| 4,569,794 A | * | 2/1986 | Smith et al. | 530/344 |
| 5,075,099 A | | 12/1991 | Srinivasan et al. | 424/1.1 |
| 5,225,180 A | | 7/1993 | Dean et al. | 424/1.1 |
| 5,250,666 A | | 10/1993 | Gustavson et al. | 530/391.5 |
| 5,443,815 A | * | 8/1995 | Dean et al. | 424/1.69 |
| 5,753,206 A | * | 5/1998 | McBride et al. | 424/1.69 |

FOREIGN PATENT DOCUMENTS

| | | |
|---|---|---|
| EP | 0 364 819 | 4/1990 |
| EP | 0 384 769 | 8/1990 |
| EP | 0 450 461 | 10/1991 |
| WO | 91/01144 | 2/1991 |
| WO | 93/10747 | 6/1993 |
| WO | 93/21962 | 11/1993 |
| WO | 94/00489 | 1/1994 |
| WO | 94/23758 | 10/1994 |
| WO | 94/28942 | 12/1994 |
| WO | 95/04540 | 2/1995 |
| WO | 95/33495 | 12/1995 |

OTHER PUBLICATIONS

Bajusz, S. et al., "Highly Potent Metallopeptide Analogues of Luteinizing Hormone–releasing Hormone", *Proc. Natl. Acad. Sci. USA* 86: 6313–6317 (1989).
Janaky, T. et al., "Analogues of Luteinizing Hormone–r-eleasing Hormone Containing Cytotoxic Groups", *Proc. Natl. Acad. Sci. USA* 89: 972–976 (1992).
Maina, T. et al., "Synthesis, Radiochemical and Biological Evaluation of $^{99m}$Tc[N4(D)Phe$^{1}$]–Octreotide, a New Octreotide Derivative with High Affinity for Somatostatin Receptors", *J. Nucl. Biol. Med.* 38: 452 (1994).
Haberberger, T. et al., "Direct Radiolabeling of the Somatostatin Analogs RC–160 and Octreotide with $^{99m}$Tc and $^{133}$Re: Initial Results with Stannous Ion Reduction", *J. Nucl. Biol. Med.* 38: 445–446 (1994).
Lister–James, J. et al., "Technetium–99m Chelate–Containing Receptor–Binding Peptides", *J. Nucl. Biol. Med.* 38: 450–451 (1994).
A. Janecka et al., "New, Highly Active Antagonists of LHRH with Acylated Lysine and p–amino–phenylalanine in Positions 5 and 6", International Journal of Peptide and Protein Research, vol. 44, No. 1, Jul. 1994, pp. 19–23.
Coy et al, Biochemical & Biophysical Research Communications, vol. 50, No. 3, 866–871, 1973.*

* cited by examiner

*Primary Examiner*—Dameron L. Jones
(74) *Attorney, Agent, or Firm*—Foley & Lardner

(57) ABSTRACT

Peptide, derivatives of leutenizing hormone releasing hormone that are capable of binding radionuclides are provided. The peptide derivatives are readily labeled with isotopes of rhenium or technetium, while retaining their ability to tightly bind LHRH receptors. Methods for preparing the labeled peptides and their use in methods of radiodiagnosis and radiotherapy are described.

22 Claims, No Drawings

RADIOMETAL-BINDING ANALOGUES OF LUTEINIZING HORMONE RELEASING HORMONE

Matter enclosed in heavy brackets [ ] appears in the original patent but forms no part of this reissue specification; matter printed in italics indicates the additions made by reissue.

BACKGROUND OF THE INVENTION

This invention relates to derivatives of leutenizing hormone releasing hormones (LHRH) in which one or more of the amino acid side chains contain chelating moieties that can tightly bind radionuclides.

Luteinizing hormone-releasing hormone (LHRH) is a decapeptide having the structure (<G)HWSYGLRPG-$NH_2$, (SEQ ID NO:1) where <G is pyroglutamic acid. LHRH controls pituitary synthesis of the gonadotropins luteinizing hormone (LH) and follicle stimulating hormone (FSH). LH and FSH control the synthesis of sex steroids in the gonads. It has been shown that analogues of LHRH, when substituted in position 6, 10, or both, display both greater and more sustained bioactivity than native LHRH. More than 3000 LHRH peptides have been evaluated both in vitro and in vivo. See, for example, Schally et al., BASIC ASPECTS; GNRH ANALOGUES IN CANCER AND IN HUMAN REPRODUCTION, Vickery & Lunenfeld eds. Vol. 1, pp. 5–31, (Kluwer Academic Publishers, Dordecht, 1989); Schally et al., ADVANCES IN GYNECOLOGY AND OBSTETRICS, GENERAL GYNECOLOGY, Belfort et al. eds., Vol. 6, pp. 3–20 (Parthenon Publishers, Carnforth, UK, 1989); Vickery et al., Endocrine Rev. 7: 115 (1986); Dutta et al., Drugs of the Future, 13:761 (1988). Several of these analogues have been used clinically, including: [D-Leu$^6$, NH-Et$^{10}$] LHRH (Vilchez-Martinez et al., Biochem. Biophys. Res. Commun. 59:1226 (1974); [D-Trp$^6$] LHRH (Coy et al., J. Med. Chem. 19:423 (1976); [D-Ser(tBu)$^6$, NH-Et$^{10}$] LHRH (Koenig et al., In: PROCEEDINGS OF THE FOURTH AMERICAN PEPTIDE SYMPOSIUM, Walter and Meienhofer eds., 883–888 (1975)); [D-Ser(tBu)$^6$, NH—NH—CO—$NH_2$$^{10}$] LHRH (Dutta et. al., J. Med. Chem. 21:1018 (1978); [D-Nal(2)$^6$]LHRH (Nestor et al., J. Med. Chem. 25:795 (1982)).

In addition, changes in position 1, 2, 3, 6 and optionally in positions 5 and 10 of the LHRH molecule can give rise to powerful antagonists. See Karten M. J. et al., Endocrine Review 7:44 (1986) and Bajusz, S. et al., Int. J. Pept. Prot. Res. 32:425 (1988). These antagonists inhibit the release of LH and FSH from the pituitary and as such, have potential as clinical agents in the imaging, diagnosis and treatment of hormone dependent cancers such as prostate, breast, ovarian, endometrial and pancreatic cancers.

The mechanism of LHRH analogue action is related, at least in part, to the fact that the density of the LHRH receptors of human tumors may be substantially greater than the LHRH receptor density of normal cells. Furthermore, the LHRH receptors of tumor cells possess a high affinity for LHRH peptides. For example, 80% of epithelial ovarian cancers have upregulated LHRH receptor densities and the receptors also have high affinities for the LHRH peptides. See Emons et al., Cancer Res. 53:5439 (1993); Irmer et al., Cancer Res. 55:817 (1955). Similarly, LHRH receptors have also been shown to be upregulated in breast cancer tumors (Fekete et al., Endocrinol. 124:946 (1989); Fekete et al., J. Clin. Lab. Anal. 3:137 (1989), endometrial cancers (Srkalovic et al., Cancer Res. 50:1841 (1990)), prostate tumors (Srkalovic et al., Endocrinol. 127:3052 (1990)), and pancreatic cancers (Schally et al., J. Steroid Biochem. Molec. Biol. 37: 1061 (1990)).

It has been shown that analogues of LHRH will selectively bind to hormone-sensitive tumors which are characterized by an overexpression of hormone receptors on the cell surface. When LHRH responsive tumors are treated with LHRH peptide analogues the analogues bind to the receptors on the cell surface and are then internalized. See Jackson et al., Cancer Treat. Rev. 16:161 (1989). Some studies have been carried out in which LHRH agonist and antagonist derivatives containing cytotoxic moieties attached to the targeting LHRH peptide have been used to deliver the cytotoxin into the cell. LHRH analogues modified with specific cytotoxic moieties may, therefore, be useful as carriers for chemotherapeutic agents. See, for example, EP 0 450 461 A2 and EP 0 364 819 A2. It has further been shown that, provided the analogues are lipophilic, various substituents can be attached to the side chain of the amino acid at position 6 of LHRH while still retaining its activity both in vitro and in vivo. (Janaky, T. et al. Proc. Natl. Acad. Sci. USA 89:972 (1992). Cytotoxic metal complexes containing platinum, nickel, and copper attached to the side chain of lysine at position 6 have demonstrated high in vitro activity in human breast tumor cells. See Bajusz, S. et al. Proc. Natl. Acad. Sci. USA 86:6313 (1989).

Some peptides either directly possesses, or are amenable to the introduction of residues that allow direct binding of radiometals to the peptide. For example, somatostatin contains a disulfide bond that, upon reduction, provides two sulfhydryl-containing cysteine side chains that can directly bind $^{99m}$Tc. See U.S. Pat. No. 5,225,180. See also WO 94/28942, WO 93/21962 and WO 94/23758. Complexes of this type tend, however, to be heterogeneous and unstable and, moreover, the use of free sulfhydryls in this manner limits the radiometals which can be used to label the peptide to those that tightly bind free S—H groups. This methods also suffers from the problem that direct binding of the metal to an amino acid side chain can greatly influence the peptide conformation, thereby deleteriously altering the receptor binding properties of the compound.

Alternatively, chelating agents can be introduced into peptide side chains by means of site-selective reactions involving particular amino acid residues. For example, the lysine residue at position 6 of LHRH has been directly acylated with a chelating group. Bajusz et al. supra. This method is inherently limited by the lack of selectivity available when more than one side chain can potentially react with the chelator, or when the peptide sequence does not contain an amino acid that can be derivatized in this way.

Most peptides either do not contain a metal-binding sequence motif or, for various reasons such as those described supra, are not amenable to suitable sequence modifications that would permit introduction of such a motif. Some means of rendering the peptide capable of binding radiometals must therefore be introduced into the peptide. A preferred approach is to attach a metal binding ligand to the peptide so that a single, stable complex is formed. The ligands used to bind metals often contain a variety of heteroatoms such as nitrogen, sulfur, phosphorous, and oxygen that have a high affinity for metals.

These ligands are typically attached at the N-terminus of the desired peptide. This allows the peptide chain to be constructed using conventional methods of peptide synthesis, followed by addition of the ligand once peptide synthesis is complete. For example, Maina et al. have described the coupling of a tetra-amine chelator to the N-terminus of a somatostatin analogue, which then allowed $^{99m}$Tc labeling of the peptide. See J. Nucl. Biol. Med. 38:452 (1994). Once again, however, application of this method is limited to those circumstances in which the N-terminus of the peptide can accommodate the presence of a (usually bulky) chelator without deleteriously affecting the binding properties of the peptide.

Bajusz et al., supra also describe the incorporation of a protected, chelate-derivatized lysine residue into a growing peptide chain during peptide synthesis. This method, however, requires the preparation of a suitably derivatized lysine derivative that also bears an α-amino protecting group that is compatible with peptide synthesis. It would clearly be preferable to be able to use protected amino acids derivatives that are commercially available for use in peptide synthesis, and to subsequently deprotect and derivatize appropriate amino acid side chains in a selective fashion.

It is apparent, therefore, that a means of attaching a chelating moiety to any predetermined position within a peptide is greatly to be desired. It is also desirable to have access to a method that would allow this chelating moiety to be coupled to the peptide at any desired stage during peptide synthesis.

SUMMARY OF THE INVENTION

It is therefore an object of the present invention to provide analogues of LHRH that can bind radionuclides while retaining the ability to specifically bind to the LHRH receptor. It is a further object of the invention to provide methods of preparing and radiolabeling analogues of LHRH that can bind radionuclides while retaining the ability to specifically bind to the LHRH receptor. It is a still further object of the invention provide diagnostic and therapeutic methods of using the radiolabeled analogues of LHRH to image or treat a tumor, an infectious lesion, a myocardial infarction, a clot, artherosclerotic plaque, or a normal organ or tissue, peptides.

These and other objects of the invention are achieved, inter alia, by providing a peptide comprising the amino acid sequence $X^1$-$X^2$-$X^3$-ser-$X^4$-$X^5$-$X^6$-$X^7$-pro-$X^8$-$NH_2$, (SEQ ID NO:2) where $X^1$ is pyroglutamic acid or D-acftylnaphthylalanine, $X^2$ is histidine or D-4-chlorophenylalanine, $X^3$ is D- or L-tryptophan or tyrosine, $X^4$ is tyrosine, leucine, or arginine, $X^5$ is a D- or L-amino acid derivative capable of chelating a radiometal, $X^6$ is leucine or tryptophan, $X^7$ is arginine or lysine, and $X^8$-$NH_2$ is glycine amide or D-alanine amide.

In accordance with one aspect of the invention $X^5$ is:

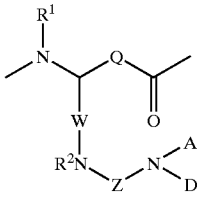

where $R^1$ is H, OH, a peptide, a sugar, a targeting molecule, lower alkyl, substituted lower alkyl, or a protecting group that can be removed under the conditions of peptide synthesis; $R^2$ is H, lower alkyl, or substituted lower alkyl; W is from 1–20 atoms long and is selected from the group consisting of cycloalkyl, aryl, or alkaryl groups, a substituted or unsubstituted alkylene chain, and a chain substituted with at least one heteroatom; Z is a peptide containing 1–5 residues, or Z is $COCH_2$ or $COCH(CH_2SP^2)$, in which $p^2$ is H or a sulfur protecting group; and A and D are the same or different, and each is selected from the group consisting of H, $COCH_2NR^3NR^4C(S)NHR^5$, $COCH_2NR^6NR^7C(S)NHR^8$, $COCH_2NR^9NR^{10}C(O)CH_2SP^2$, $CONR^{11}NR^{12}C(O)CH_2SP^2$, $NR^{13}C(S)NHR^{14}$, or $COCH_2NR^{15}COCH_2SP^2$, $R^3$, $R^4$, $R^6$, $R^7$, $R^9$, $R^{10}$, $R^{11}$,$R^{12}$, $R^{13}$, and $R^{15}$ are the same or different, and each represents H, lower alkyl, or substituted lower alkyl, and $R^5$, $R^8$, and $R^{14}$ are the same or different and each is H, lower alkyl, substituted lower alkyl, aryl, or substituted aryl.

In a preferred embodiment of the invention $X^5$ is selected from the group consisting of:

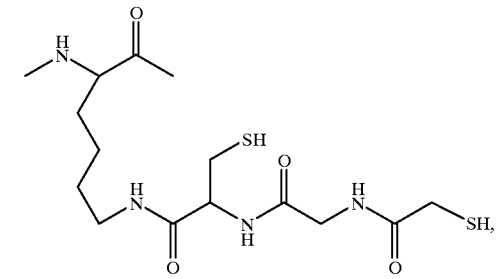

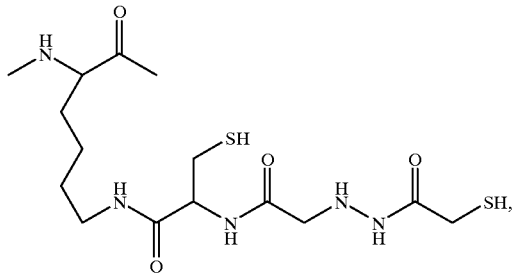

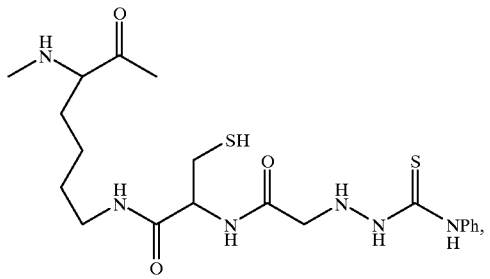

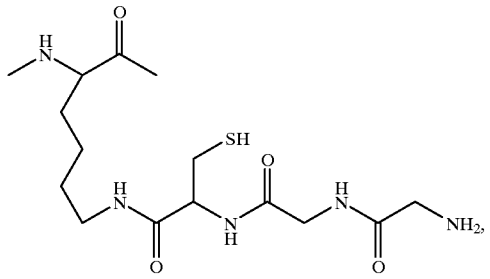

-continued

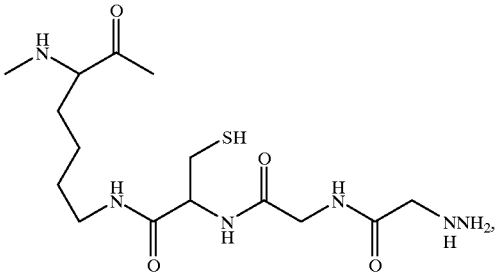

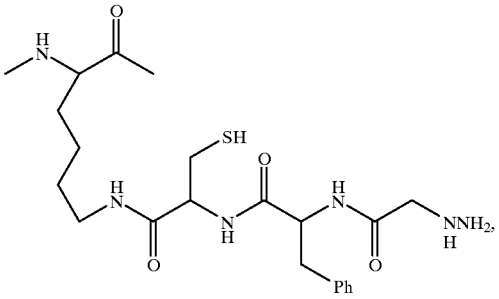

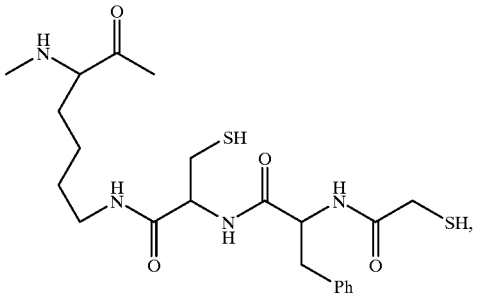

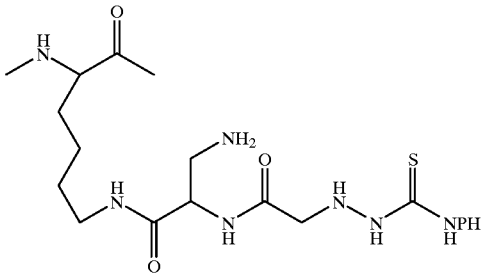

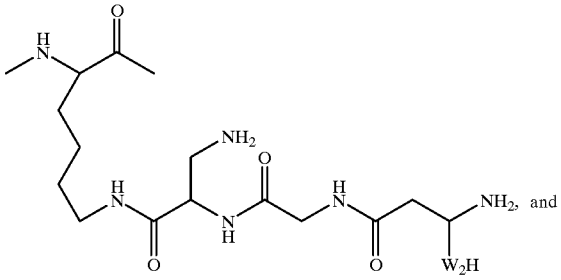

-continued

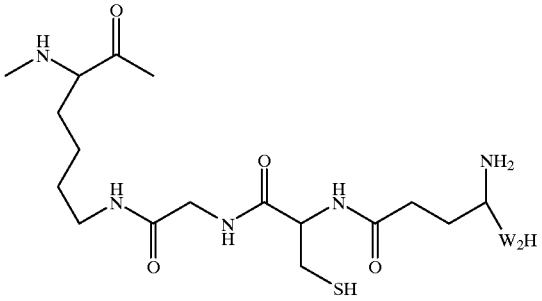

In accordance with another aspect of the invention there are provided peptides in which $X^1$ is pyroglutamic acid, $X^2$ is histidine, and $X^5$ is glycine amide. In preferred embodiments of this aspect of the invention $X^3$ is tyrosine, $X^4$ is leucine, $X^6$ is tryptophan, and $X^7$ is lysine. In other preferred embodiments of this aspect of the invention $X^5$ is

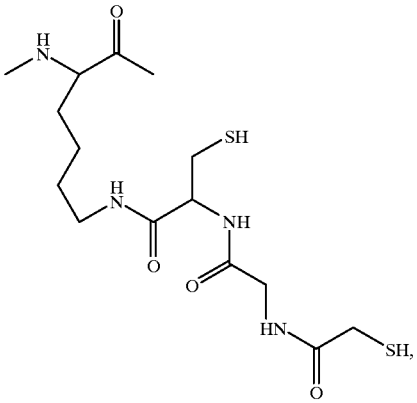

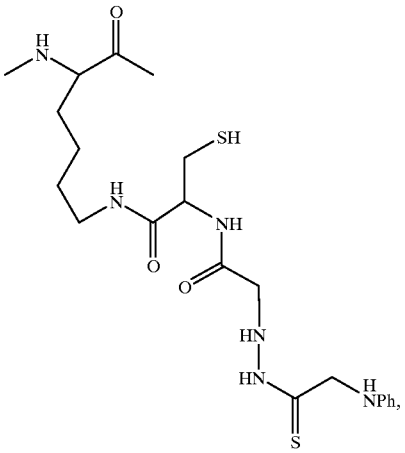

-continued

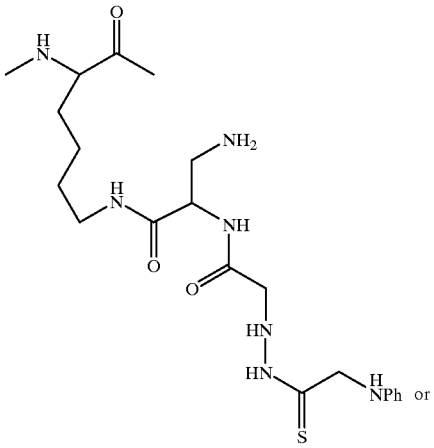

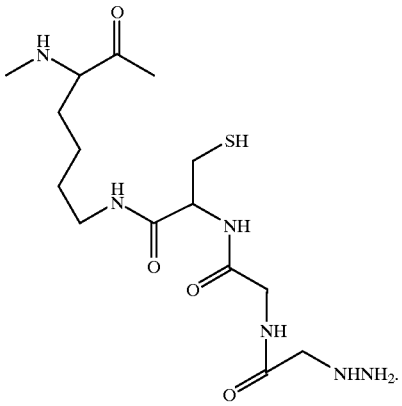

In other preferred embodiments of this aspect of the invention, $X^3$ is tryptophan, $X^4$ is tyrosine, $X^6$ is leucine, $X^7$ is arginine, and $X^5$ is

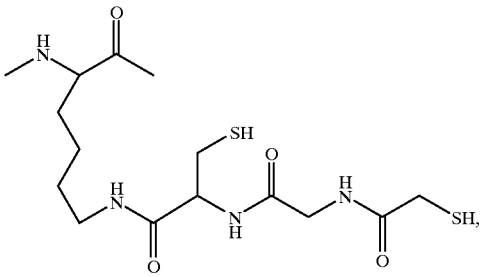

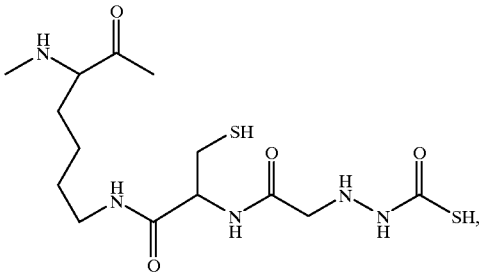

-continued

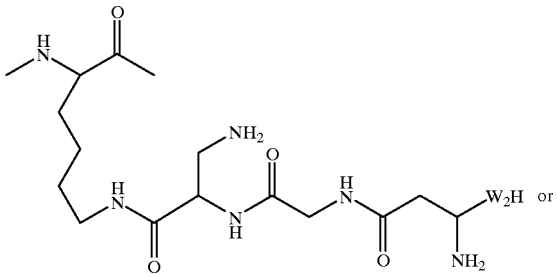

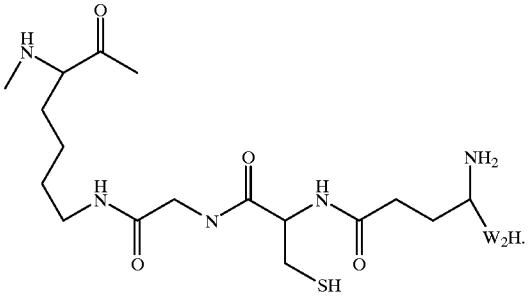

In accordance with still another aspect of the invention there is provided peptides in which $X^1$ is D-acetylnaphthylalanine, $X^2$ is D-4-chlorophenylalanine, $X^3$ is D-tryptophan, $X^4$ is arginine, $X^6$ is leucine, $X^7$ is arginine, and $X^8$—$NH_2$ is D-alanine amide. In preferred embodiments $X^5$ is

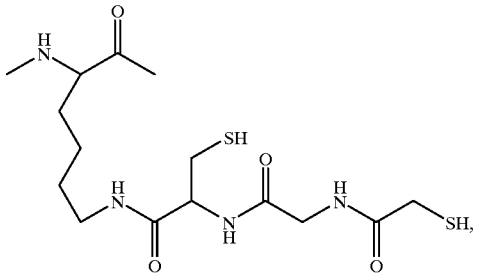

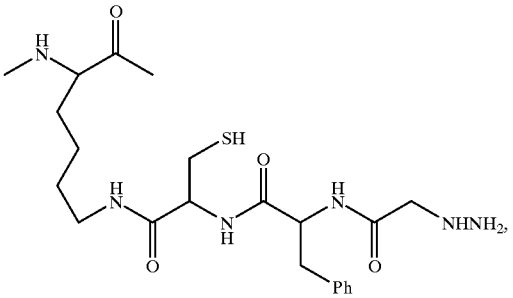

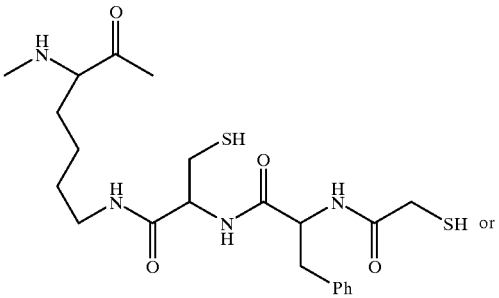

-continued

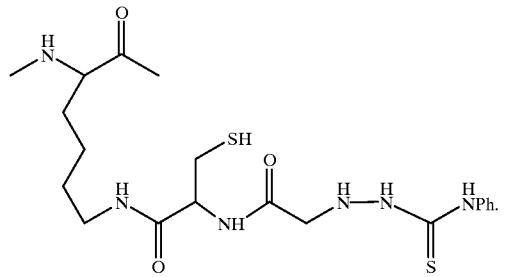

In accordance with yet another aspect of the invention there are provided peptides in which $X^1$ is D-acetylnaphthylalanine, $X^2$ is D-4-chlorophenylanine, $X^3$ is D-tryptophan, $X^4$ is arginine, $X^6$ is tryptophan, $X^7$ is lysine, and $X^8$—$NH_2$ is glycine amide.

In accordance with a yet further aspect of the invention there is provided a method of preparing a metal-chelating composition, comprising contacting a solution of a peptide with stannous ions, where the has the amino acid sequence described above, and then contacting this solution with a radionuclide and recovering the radiolabeled peptide. In a preferred embodiment the radionuclide is selected from $^{188}$Re- or $^{186}$-perrhenate and $^{99}$Tc-pertechnetate.

In accordance with yet another aspect of the invention there are provided peptides that specifically bind cells or tissues that express LHRH receptors.

In accordance with another aspect of the invention there is provided a method of imaging a tumor, an infectious lesion, a myocardial infarction, a clot, artherosclerotic plaque, or a normal organ or tissue, comprising administering to a human patient a radiolabeled peptide that specifically binds to cells or tissues that express LHRH receptors, together with a pharmaceutically acceptable carrier, and, after a sufficient time for the radiolabeled peptide to localize and for non-target background to clear, the site or sites of accretion of the radiolabeled peptide are detected by an external imaging camera, wherein the radiolabeled peptide is prepared by the method described above.

DETAILED DESCRIPTION

The present invention provides analogues of leutenizing hormone releasing hormone (LHRH) that are capable of binding radionuclides. These analogues are prepared by site-specifically introducing radionuclide-chelating amino acid derivatives into peptides that are synthesized by solid-phase or solution phase methods.

The synthesis of the analogues involves the use of differentially protected bis-amino acid derivatives in which either amino function can be selectively deprotected. These derivatives are introduced into a growing peptide chain during peptide synthesis by conventional peptide coupling methodology. One of the amino functions is then selectively deprotected, allowing subsequent coupling of either a chelating molecule, or addition of further amino acid residues to continue the peptide synthesis.

If peptide synthesis is continued, selective deprotection of the second amino group of the bis-amino acid can be accomplished at any point during the peptide synthesis to introduce the chelating moiety. Once the peptide synthesis is complete, cleavage, deprotection, and purification affords the peptide derivative. This derivative is then labeled with a radiometal for use in radiodiagnostic and radiotherapeutic applications.

Alternatively, if the chelating molecule is coupled to the deprotected amino group first, the second step is to deprotect the other amino group and continue with the peptide synthesis. Final cleavage, deprotection and purification steps yield the pure peptide derivative, which is then radiolabeled as before.

The radiometal chelating peptides of the present invention are stable in blood and other bodily fluids and tissues. Both the reagents and the conditions in the present method are greatly simplified over those in the prior art, and the labeled peptides are particularly suitable for radiodiagnostic and radiotherapy applications using technetium or rhenium labeling.

The approach outlined above allows the placement of a radiometal-binding amino acid anywhere in the LHRH peptide sequence. Placing the chelating moiety on an amino acid side-chain, rather than the N-terminus of a peptide, has the added advantage of spatially distancing the metal complex from the peptide backbone, thereby minimizing the effect of the metal complex on the peptide conformation.

It is known that peptide conformation is greatly influenced by charge and hydrophilic/hydrophobic interactions, and it is therefore important to consider these variables when designing a chelating ligand to be used in peptides. It is preferred that a variety of chelating complexes of varying charge and hydrophilicity are prepared and tested to select the metal-complexed LHRH peptide that displays the optimum combination of target selectivity and chelate stability.

The radiolabeled LHRH peptides of the present invention bind specifically to a diseased cell or tissue that exhibits both a high LHRH receptor density and high affinity for LHRH. The radioactivity of the radionuclide allows diagnosis and/or treatment of the tumor or diseased tissue. The invention also includes pharmaceutical compositions comprising an effective amount of at least one of the radiolabeled peptides of the invention, in combination with a pharmaceutically acceptable sterile vehicle, as described, for example, in Remington's Pharmaceutical Sciences; Drug Receptors and Receptor Theory, 18th ed., Mack Publishing Co., Easton, Pa. (1990). The invention also includes kits for labeling peptides which are convenient and easy to use in a clinical environment.

Design and Synthesis of Peptides Incorporating Chelating Amino Acid Derivatives The peptides of the invention contain radiometal-chelating amino acid derivatives that are characterized by the presence of at least one thiol or thiocarbonyl group, and at least one nitrogen present as either a tertiary amine or a secondary amide. The sulfur and nitrogen atoms are suitably disposed to form a multidentate ligand capable of tightly and preferentially binding reduced radionuclide. These amino acid derivatives are incorporated into peptides that bind tightly to the LHRH receptor. These peptides can be represented generally by the formula:

$$X^1\text{-}X^2\text{-}X^3\text{-ser-}X^4\text{-}X^5\text{-}X^6\text{-}X^7\text{-pro-}X^8\text{-}NH^2 \text{ (SEQ ID NO:2)}$$

where $X^1$ is pyroglutamic acid or D-acetylnaphthylalanine;

$X^2$ is histidine or D-4-chlorophenylalanine;

$X^3$ is D- or L-tryptophan or tyrosine, $X^4$ is tyrosine, leucine, or arginine, $X^5$ is a radiometal-chelating amino acid as described below;

$X^6$ is leucine or tryptophan;

$X^7$ is arginine or lysine; and $X^8$—$NH_2$ is glycine amide or D-alanine amide.

The radiometal-chelating amino acid derivatives contemplated by the invention can be represented by the general formula:

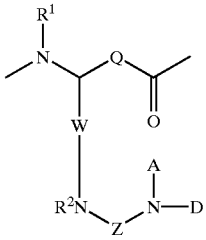

is which $R^1$ represents H, OH, a peptide, a sugar, a targeting molecule, lower alkyl, substituted lower alkyl, or a protecting group that can be removed under the conditions of peptide synthesis, $R^2$ is H, lower alkyl, or substituted lower alkyl, W is from 1–20 atoms long and is selected from the group consisting of cycloalkyl, aryl, alkaryl, a substituted or unsubstituted alkylene chain, and a chain substituted with at least one heteroatom, Z is a peptide containing 1–5 residues, or Z is $COCH_2$ or $COCH(CH_2SP^2)$, in which $P^2$ is H or a sulfur protecting group, A and D are the same or different, and each is selected from the group consisting of H, $COCH_2NR^4C(S)NHR^5$, $COCH_2NR^6NR^7C(S)NHR^8$, $COCH_2NR^9NR^{10}C(O)CH_2SP^2$, $CONR^{11}NR^{12}C(O)CH_2SP^2$, $NR^{13}C(S)NHR^{14}$, or $COCH_2NR^{15}COCH_2SP^2$, $R^3$, $R^4$, $R^6$, $R^7$, $R^9$, $R^{10}$, $R^{11}$, $R^{12}$, $R^{13}$, and $R^{15}$ are the same or different, and each represents H, lower alkyl, or substituted lower alkyl, and $R^5$, $R^8$, and $R^{14}$ are the same or different and each is H, lower alkyl, substituted lower alkyl, aryl, or substituted aryl.

Representative embodiments of radiometal-chelating amino acid derivatives of the invention are:

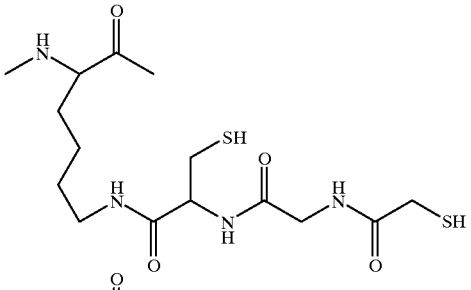

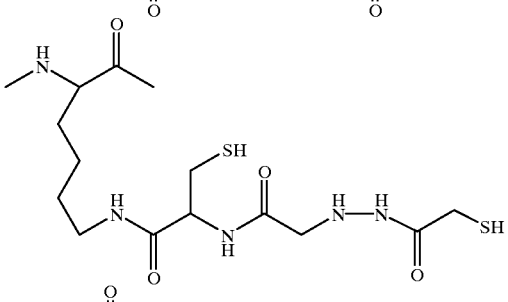

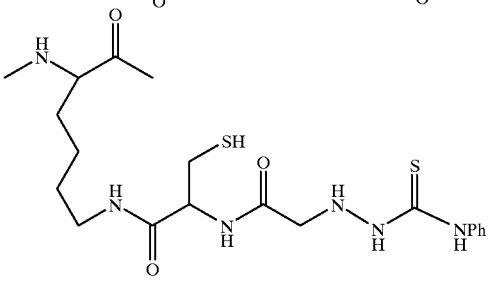

-continued

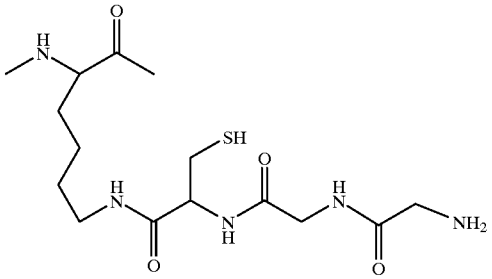

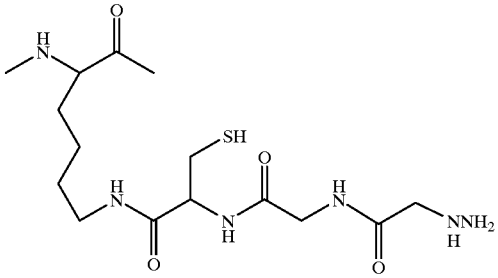

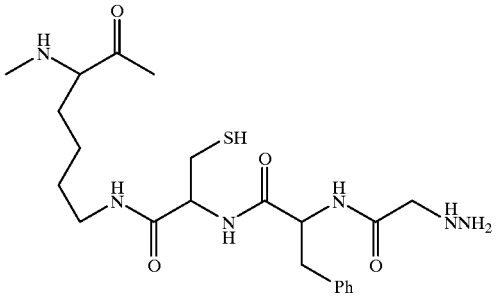

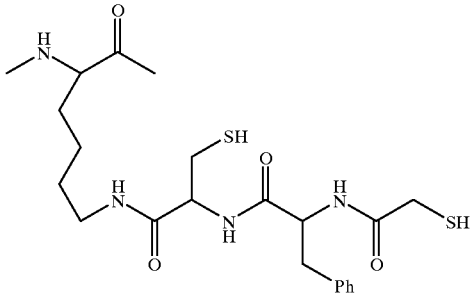

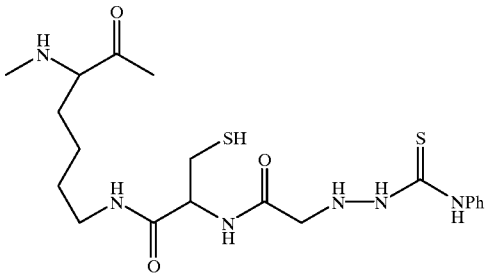

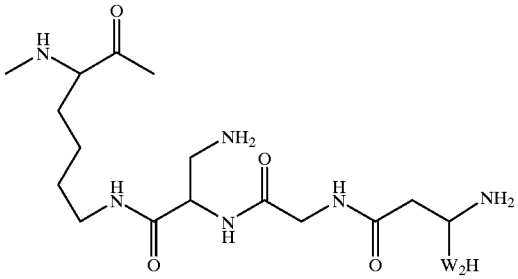

-continued

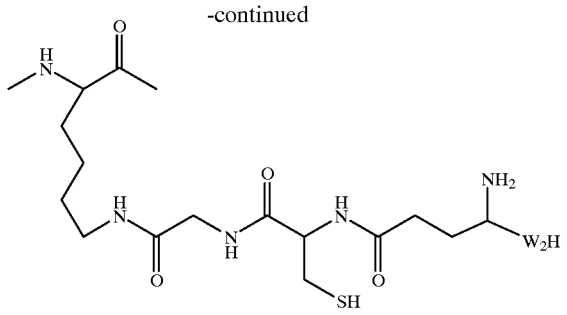

Each of the chelating amino acids of the invention can be prepared by methods well known to the skilled practitioner in the art of organic synthesis. Detailed protocols for the synthesis of representative chelates are given in the examples found below.

The chelating amino acids are constructed from subunits that are linked together by simple coupling or condensation reactions, such as the condensation of an amino, hydrazino, or hydrazido function with an activated carboxyl group, or reductive amination reactions between amines and aldehydes. As used herein the term "condensation" is intended to encompass reactions that couple together subunits of the chelating moiety, and thus encompasses reactions such as reductive amination in addition to reactions that conform to the classical definition of a condensation reaction.

Following a condensation reaction, additional functional groups on the subunit may be deprotected to allow additional condensation reactions. For example, a second subunit carrying a free carboxyl group and a protected amino function can be condensed with an amino, hydrazino, or hydrazido function on a first subunit. The amino function on the second subunit moiety can then be deprotected and further coupled to a third subunit.

Methods of activating carboxyl groups for such condensation reactions are well known to those of skill in the art of organic synthesis and peptide synthesis, and include the use of active esters and of carbodiimide coupling agents. Suitable protecting groups are used for protecting functions on the subunits when the reactivity of the functions is incompatible with a reaction used to join the subunits. Protecting groups for both amino and carboxylic acid functions are well known in the art. See, for example, Greene, supra. The subunits used to construct the chelate are either readily prepared by method well known in the art, or are commercially available from suppliers such as Advanced ChemTech (Lexington, Ky.), Milligen (Burlington, Mass.), Applied Biosystems (Foster City, Calif.), or Aldrich Chemical Corp. (Milwaukee, Wis.).

The condensation reactions used to link together the subunits can either be carried out prior to peptide synthesis, or during the peptide synthesis process. When the amino acid derivative is assembled from its subunits prior to peptide synthesis, α-amino and α-carboxyl functions must be suitably protected in a manner that is subsequently compatible with selective deprotection and activation of these functionalities for peptide synthesis. Examples of such protecting groups are well known in the art, and include the fluorenemethyloxycarbonyl (Fmoc), benzyloxycarbonyl (Cbz), $^t$butoxycarbonyl (Boc), and allyloxycarbonyl (alloc) groups for amino protection. Groups for carboxyl protection include the methyl (Me), benzyl (Bn), $^t$butyl ($^t$Bu), and allyl esters, respectively. The amino and carboxyl protecting groups must be selected such that each group can be selectively deprotected in the presence of the other. This precludes, for example, use of the Cbz group for protection of the amino function in the presence of a carboxyl group protected as a benzyl ester. See Greene, supra. In a preferred embodiment, the α-amino group is protected as an Fmoc group, and the α-carboxyl group is a methyl ester. The thiol protecting group used in the compounds of the invention can be any organic or inorganic group which is readily removed under mild conditions to regenerate the free sulfhydryl in the presence of the protein. Suitable protecting groups are listed in Greene, PROTECTIVE GROUPS IN ORGANIC SYNTHESIS (Wiley Interscience, NY. 1981) pp. 193–217. Examples of suitable protecting groups include trityl groups, thiol esters, thiocarbamates and disulfides. In a preferred embodiment the thiol protecting group is a trityl group. Those skilled in the art are familiar with the procedures of protecting and deprotecting thiol groups. For example, benzoate thioesters may be deprotected under mild and selective conditions using hydroxylamine.

Once assembly of the protected chelating moiety is complete, the α-carboxy function is deprotected and coupled to the amino terminus of the peptide chain using conventional methods of peptide synthesis. See Bodanszky et al., THE PRACTICE OF PEPTIDE SYNTHESIS (Springer Verlag, Heidelberg, 1984).

When the amino acid derivative is assembled from its subunits during peptide synthesis, the peptide chain is assembled by conventional solid phase synthesis until the point where the derivative is to be incorporated. The differentially protected bis-amino acid is then coupled to the amino terminus of the peptide chain, followed by selective deprotection of one of the amino groups of the derivative.

If the α-amino function is deprotected first, all or part of the remaining amino acid residues are then coupled to the peptide chain in the conventional manner. The side chain amino function of the derivative is then deprotected, and the chelating moiety is assembled as described above. The complete peptide can then be deprotected and purified by standard methods.

If the side chain amino function is deprotected first, the chelating moiety is then assembled as described above, followed by deprotection of the α-amino group. Peptide synthesis is then completed in the conventional manner as described above.

Once peptide synthesis is complete the fully protected peptide is deprotected and purified. Methods for deprotection and purification of synthetic peptides are well known in the art. See, for example, Bodanszky, supra. If the peptide was synthesized by solid phase techniques the peptide must also be cleaved from the resin used as the solid support for the synthesis. Methods for achieving this cleavage are also well known in the art. Methods for purifying synthetic peptides such as those of the present invention are also well known to those of skill in the art. Such methods include, for example, ion exchange, gel filtration chromatography, and reversed phase high pressure liquid chromatography (RP-HPLC). In a preferred embodiment of the invention the peptide is purified by RP-HPLC using a preparative scale octadecylsilane (C18) silica column packing, eluting with a gradient of acetonitrile in 0.1% trifluoroacetic acid (TFA). The purity of the peptide can be confirmed by standard methods such as analytical RP-HPLC or capillary electrophoresis. The identity of the peptide can be confirmed by NMR spectroscopy, or in a preferred embodiment of the invention, by mass spectrometry.

Chelation of Radiometals by Peptides Incorporating Metal-Chelating Amino Acid Derivatives Once a peptide incorporating a metal-chelating amino acid derivative has been synthesized and purified it can be stored for later use, or it can be reacted with radionuclide for immediate use in radioimmunotherapy or radioimmunodiagnostic procedures. If the peptide is to be stored for later use, the free thiol groups are preferably protected against oxidation. In a preferred embodiment of the invention this can be achieved by storing the peptide under an inert atmosphere, or alternatively the peptide can be stored in the presence of a reducing agent such as β-mercaptoethanol. Storage of the peptide in a form bearing free sulfhydryl groups can also be achieved by admixing the conjugate with the agent to be used for reducing the radionuclide. For example, the added reducing agent is a $tin^{II}$ salt. The salt can be generated as required from tin metal, e.g., foil, granules, powder, turnings and the like, by contact with aqueous acid, e.g., Hcl and is usually added to the peptide in the form of $SnCl_2$, advantageously in a solution that is about 0.1 mM in HCl. The resulting mixture can be stored as a frozen solution, or preferably is stored as a lyophilized powder. Storage of the conjugate in the presence of a reducing agent in this form is advantageous because it not only prevents reoxidation of the thiol functions, but also dispenses with the requirement of an additional step to reduce the radionuclide, as discussed below.

The peptide or peptide-reducing agent mixture can be assembled into a single vial or kit for use in performing the radiolabeling method of the present invention. A radionuclide then can be added to the kit as needed to provide a radiolabeled peptide. The single vials or kits of the present invention are designed to contain the appropriate peptide for any particular diagnostic or therapeutic procedure.

In accordance with the present method, the vials or kits advantageously are sealed and provided with a mechanism of introducing or withdrawing reagents under sterile or semi-sterile conditions. Preferably, a vial containing a port for syringe injection is used in the present method. The reagents in the vials or kits typically are provided in aqueous, frozen or lyophilized form. In one embodiment the reagents can be stored at low temperature, e.g., in the refrigerator, for several days to several weeks, preferably at a pH of about 3.5–5.5, more preferably at pH 4.5–5.0, advantageously under an inert gas atmosphere, e.g., nitrogen or argon.

It also is within the scope of the present invention to provide the reagents in lyophilized form for ease of storage and stabilization. This is advantageously effected at a pH of about 5.5, from a solution of a volatile buffer, e.g., ammonium acetate, and preferably also in the presence of a stabilizer to prevent aggregation, e.g., a sugar such as trehalose or sucrose. Such lyophilization conditions are conventional and well known to the ordinarily skilled artisan.

The labeling procedure of the present invention then can be performed simply by adding the radioisotope directly from the generator e.g., in the form of aqueous sodium pertechnetate, to the peptide or the reducing agent-chelating peptide mixture. The contents of the vial then are mixed and incubated for time sufficient to effect labeling of the peptide. The duration and condition of incubation are not crucial, but incubation typically is carried out for a period of time sufficient to obtain substantially 100% binding of radioisotope to the protein. As noted above, different radionuclides require more or less extensive reducing conditions, and thus the length of the incubation will also depend on the identity of the radionuclide used. "Substantially 100% binding" denotes greater than 98% radionuclide incorporation, advantageously, greater than 99% and more advantageously 100% incorporation. Usually, the incubation is conducted for a period of time of from about 0.1 to about 60 minutes, but in a preferred embodiment is conducted for about 1 to about 5 minutes. The radiolabeled peptide then can be withdrawn from the vial, and immediately used since further separation or purification is not required.

In a preferred embodiment of the invention the labeling of the peptide chelate is carried out by mixing the peptide with a radiometal-glucoheptonate complex to effect transchelation from the glucoheptonate to the peptide. This method is particularly preferred when the radiometal is technetium-99. This procedure is conveniently carried out using a Glucoscan kit (E. I. DuPont de Nemours, Inc. Boston, Mass.). The labeling is preferably carried out at room temperature in saline solution. If the peptide is not very soluble in saline a solubilizing agent such as ethanol or 2-hydroxypropyl-b-cyclodextrin may be added. The labeling may also be carried out at elevated temperatures, such as 50°–100° C., in order to increase the rate of the labeling reaction. Protocols for labeling peptides of the invention with technetium and rhenium are illustrated further in Examples 9 and 10 infra.

Pertechnetate for labeling peptides with $^{99m}Tc$ generally is obtained from a commercially available generator, most commonly in the form of $NaTcO_4$ in a saline solution. Other forms of pertechnetate may be used, with appropriate modification of the procedure, as would be suggested by the supplier of a new form of generator or as would be apparent to the ordinarily skilled practitioner. Pertechnetate is generally used at an activity of about 0.2–10 mCi/ml in saline, e.g., 0.9% ("physiological") saline, buffered at a pH of about 3–10, preferably at about 4.5–9.0. Suitable buffers include, e.g., acetate, tartrate, citrate, phosphate and the like.

Throughout this description, the phrases "reduced pertechnetate" or "reduced perrhenate" denote the species of technetium or rhenium ion formed by reduction of pertechnetate or perrhenate with, for example, stannous ion, and chelated by the thiol group(s). It is generally thought that reduced pertechnetate is in the form of Tc(III) and/or Tc(IV) and/or Tc(V) in such chelates, and that reduced perrhenate is in the form of Re(III) and/or Re(IV) and/or Re(V), but higher or lower oxidation states and/or multiple oxidation states are included within the scope of the present invention.

Rhenium is found just below technetium in the periodic table, has the same outer shell electronic configuration and therefore is expected to have very similar chemical properties, especially with respect to its behavior with analogous compounds. The skilled practitioner is capable of modifying the present invention based on the disclosure of technetium labeling to achieve efficient rhenium labeling.

The radioisotope Rc-186 is attractive for radioimmunotherapy and can also be used for imaging. Re-188 is a generator-produced beta and gamma emitter with a half-life of about 17 hours and is suitable for imaging and therapy. Complexation of the peptides of the invention with rhenium is carried out in essentially the same manner as is described for technetium, supra.

For preliminary studies such as measurement of affinity constants, in vitro screening, etc. for metal-bound peptides, non-radioactive rhenium is conveniently used. This allows the properties of the peptide-rhenium complexes to be studied without the risks associated with the handling of radioactive rhenium. Use of non-radioactive rhenium also acts as a convenient model for the behavior of technetium complexes of the peptides, since no non-radioactive isotope of technetium exists, and the chemical properties of rhenium and technetium are very similar.

Once the peptide derivative has been radiolabeled it is important to confirm that the radiolabeled conjugate retains the receptor binding specificity of native LHRH. Methods for determining the activity of LHRH analogues are well known in the art. For example, a competitive cell binding assay can be used. Target cells, for example human breast adenocarcinoma cell lines MCF-7, SK-BR-3, and MDA-MB-231 (American Type Culture Collection, Rockville, Md.) are used in a standard assay format in which cells are treated with different concentrations of the labeled or unlabeled peptides of the invention in the presence of LHRH (Amersham Life Science, Arlington Heights, Ill.). The radioactivity associated with the cells is counted and the concentration of the unlabeled LHRH that causes 50% inhibition of the binding of the labeled LHRH analogues is determined. The equilibrium association constant, $K_a$, and the total number of receptor sites per cell may be determined by Scatchard analysis. See Fersht, ENZYME STRUCTURE AND MECHANISM, 2d ed. (W. H. Freeman, London, 1985).

The ability of the radiolabeled peptide to retain radiolabel in physiological solution can be measured using techniques essentially similar to those used for radiolabeled antibodies. See Hnatowich et al., J. Nucl. Med. 34:109 (1993). For example, assays can be used to determine the ability of the peptide to retain radiolabel in saline and serum solution, and in the presence or absence of material such as human serum albumin, DTPA, DOTA, cysteine and glutathione.

The in vivo bioactivity of the radiolabeled peptides of the invention is readily determined by standard biodistribution studies in animal models, using for example, MCF-7 tumor cells grown in estrogen-dosed nude mice. In these studies it is useful to determine the receptor capacity of mice bearing LHRH-binding tumors in order to estimate the quantities of radiolabeled peptide required for imaging and/or therapy experiments. For this purpose, carrier free $^{125}$I LHRH (~2000 Ci/mmol, Amersham Life Science) is injected into mice bearing MCF-7 tumors, and the mice are sacrificed at defined time intervals post-injection. The major organs, as well as the blood, and the tumor are removed, weighed, and counted to determine the percent injected dose per gram (% ID/g) in each organ. Increasing amounts of unlabeled LHRH are then mixed with the $^{125}$I LHRH and injected into the tumor-bearing nude mice, which are sacrificed as above, at the same time points determined from the previous experiment. This allows the determination of the LHRH receptor capacity in the nude mouse model.

Radiolabeled peptides that show in vitro receptor affinity as determined above are then screened in the MCF-7 nude mouse model. The Tc-99m labeled peptide can be purified by HPLC to obtain the peptide carrier free metal complex for these studies if the LHRH receptor capacity is too low to tolerate the presence of excess peptide. The biodistribution of the radiolabel is monitored on, for example, for $^{99m}$Tc-labeled peptides, a gamma camera equipped with a pinhole collimator. In the initial screen the animals will be sacrificed after 4 hr and the biodistribution determined as described above. Peptides that display tumor uptake and a significant tumor to nontarget profile are then tested in a blocking assay using LHRH to determine of the tumor uptake in vivo is specific. The tumor to nontarget profile of a radiolabeled peptide of the invention is significant if the size and location of the tumor can be determined under standard imaging conditions using the peptide.

E. Administration of the radiolabeled peptide for diagnosis and therapy.

The peptides of the invention may be used for diagnosis or therapy of any physiological condition in which cells or tissue express high numbers of LHRH receptors, or express LHRH receptors of high affinity, or both. The peptides may advantageously be stored in kits as described above. These may be frozen or lyophilized in sterile containers under an inert gas atmosphere, and are advantageously gently thawed just prior to use. The kits are conveniently supplemented with sterile vials of buffers, saline, syringes, filters and other auxiliaries to facilitate preparation of injectable preparations ready for use by the clinician or technician. The clinician or technician can then conveniently add a solution of a suitable radionuclide just prior to administration to a patient.

Generally, the dosage of administered labeled peptide will vary depending upon such factors as the patient's age, weight, height, sex, general medical condition, and previous medical history. Typically, it is desirable to provide the recipient with a dosage of protein which is in the range of from about 1 pg/kg to 10 $\mu$mg/kg (amount of agent/body weight of patient), although a lower or higher dosage may also be administered.

For therapeutic applications, about 0.1–500 micrograms of radiolabeled peptide will be administered, normally daily for a period of several days. Administration of radiolabeled peptides to a patient can be intraveneous, intraarterial, intraperitoneal, intramuscular, subcutaneous, intrapleural, intrathecal, by perfusion through a regional catheter, or by direct intralesional injection. Administration by injection may be by continuous infusion, or by single or multiple boluses.

The radiolabeled peptides of the present invention can be formulated according to known methods to prepare pharmaceutically useful compositions, whereby they are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 18th Ed. (1990).

For purposes of radiotherapy, a radiolabeled peptide and a pharmaceutically acceptable carrier are administered to a patient in a therapeutically effective amount. A combination of a radiolabeled peptide and a pharmaceutically acceptable carrier is said to be administered in a "therapeutically effective amount" if the amount administered is physiologically significant. An agent is physiologically significant if its presence results in a detectable change in the physiology of a recipient patient.

Additional pharmaceutical methods may be employed to control the duration of action of a radiolabeled peptide in a therapeutic application. Control release preparations can be prepared through the use of polymers to complex or adsorb the protein. For example, biocompatible polymers include matrices of poly(ethylene-co-vinyl acetate) and matrices of a polyanhydride copolymer of a stearic acid dimer and sebacic acid. Sherwood et al., Bio/Technology 10:1446–1449 (1992). The rate of release of a peptide from such a matrix depends upon the molecular weight of the peptide, the amount of peptide within the matrix, and the size of dispersed particles. Saltzman et al., Biophysical. J. 55:163–171 (1989); and Sherwood et al., supra. Other solid dosage forms are described in REMINGTON'S PHARMACEUTICAL SCIENCES, 18th Ed. (1990).

The present invention, thus generally described, will be understood more readily by reference to the following examples, which are provided by way of illustration and are not intended to be limiting of the present invention.

EXAMPLES

Example 1

Synthesis of $N^{\alpha}$Alloc-Ne-Fmoc-L-Lycine $N^{e}$-Fmoc-L-Lysine (10.00 g, 27.1 mmol, 100 mol %, Bachem Biosciences, Inc.) was suspended in dioxane (100 ml) and $Na_2CO_3$ (1M, 33 ml) to form a milky suspension. Allyl chloroformate (3.2 ml, 30.2 mmol, 111 mol %) was added to dioxane (10 ml) and this solution was added dropwise to the suspension of $N^{e}$-Fmoc-L-Lysine over 10 min. Sodium carbonate, (1M, 20 ml) was added in two portions and an additional quantity of allyl chloroformate (0.3 ml) was added. The reaction was stirred at room temperature for 16 hours. The volatile solvents were removed under reduced pressure and the residue was washed with diethyl ether (50 ml). The residual liquid was then acidified with HCl (1M) and extracted with ethyl acetate (2×150 ml). The organic layers were combined, washed with saturated NaCl (50 ml), dried over $Na_2SO_4$, evaporated under reduced pressure to obtain a crude oily product (16 g). The crude product was dissolved in ether (100 ml) and a white solid formed and was removed by filtration. The solvent from the filtrate was removed under reduced pressure to afford a viscous pale yellow oil (8.34 g, 68% yield) which eventually formed a glassy solid.

Example 2

Synthesis of 2-(triphenylmethylmercapto)acetyl hydrazide 2-(triphenylmethylmercapto) acetic acid (20.35 g, 60.9 mmol, 100 mol %) was dissolved in anhydrous THF (150 ml) and cooled in an ice water bath. t-Butylcarbazate (8.61 g, 65.1 mmol, 107 mol %) was added to the reaction solution followed by diisopropylcarbodiimide (10.0 ml, 63.9 mmol, 105 mol %). The reaction was allowed to warm slowly to room temperature and stirred for 28 hours. The reaction mixture was filtered to remove the white precipitate that had formed and the filtrate was concentrated to a white foam by removal of the solvent under reduced pressure. This material was dissolved in chloroform (75 ml). Then acetic acid (75 ml) was added followed by the addition of borontrifluoride etherate (10.0 ml, 81 mmol, 134 mol %). The reaction was stirred at room temperature for 6 hours and then quenched by pouring the reaction mixture into water (200 ml) containing sodium acetate (30 g). This mixture was extracted with chloroform (2×100 ml). The organic layers were combined, washed with saturated NaCl solution (150 ml), dried over $Na_2SO_4$ and filtered. The solvent was removed under reduced pressure to obtain a pale gold oil which solidified on standing. The solid was suspended in 1:1 diethylether/hexanes (200 ml) and collected by filtration. The solid was washed with an additional quantity of 1:1 diethylether/hexanes (100 ml) and dried to afford the desired product (15.44 g, 73% yield) having ESMS MH+calculated 349, observed 349.

Example 3

Synthesis of $N^{\beta}$-[2-(triphenylmethylthio) acetyl]azaglycine

Glyoxylic acid monohydrate (0.59 g, 6.41 mmol, 110 mol %) was dissolved in methanol (20 ml) and 2-(triphenylmethylmercapto)acetyl hydrazide (2.03 g, 5.82 mmol, 100 mol %) was added. Dioxane (20 ml) was added to the cloudy reaction mixture and the reaction was stirred at room temperature for 18 hours. Sodium borohydride (1.76 g) was added to the reaction mixture and after 30 minutes, another quantity of sodium borohydride (0.60 g) was added. The reaction was stirred for 3 hours at room temperature, then quenched by pouring the reaction mixture into HCl (1M, 60 ml). The mixture was extracted with ethyl acetate (2×50 ml). The organic layers were combined, washed with saturated NaCl solution (40 ml), dried over $Na_2SO_4$, filtered, and concentrated under reduced pressure on the rotary evaporator to afford a solid (2.5 g) having ESMS $MH^+$ calculated 407, found 407.

Example 4

Synthesis of $N^{\Delta}$-Boc-Nβ-[2-(triphenylmethylthio)acetyl] azaglycine $N^{\beta}$-[2-(triphenylmethylthio)acetyl]azaglycine (2.39 g, 5.89 mmol, 100 mol %) was dissolved in dioxane (50 ml). Di-t-butyl dicarbonate $(BOC)_2O$, (2.07 g, 9.48 mmol, 161 mol %) was added to the reaction solution followed by the addition of $Na_2CO_3$ (1M, 15 ml). This mixture was stirred at room temperature for 15 minutes, then additional quantities of $Na_2CO_3$ (1M, 10 ml) and $(BOC)_2O$ (1.41 g) were added. The solution was stirred at room temperature for 18 hours then reacted with NaOH (6M, 3 ml) and $(BOC)_2O$ (1.4 g) for 1 hour. The crude reaction mixture was then acidified to pH 3 with citric acid (1M) and extracted with ethyl acetate (200 ml). The organic layer was washed with saturated sodium chloride solution (60 ml), dried over $Na_2SO_4$, filtered and concentrated under reduced pressure to obtain the crude product. The crude product was dissolved in ether and diluted to obtain a 1:1 mixture with hexanes causing a white precipitate to form. The white solid was collected by filtration to obtain the desired product (1.48 g, 50% yield) having ESMS $MH^+$ calculated 507, found 507.

Example 5

Synthesis of 2-(4-Phenyl-3-thiosemicarbazidyl)acetic acid

4-Phenyl-3-thiosemicarbazide (6.02 g, 36 mmol, 100 mol %) was suspended in methanol (40 ml). Glyoxylic acid monohydrate (3.32 g, 36.1 mmol, 100 mol %) was added and the reaction was stirred at room temperature for 2 hours. Sodium borohydride (1.50 g) was added carefully, and the reaction mixture bubbled very vigorously. The reaction mixture was stirred at room temperature for 1 hour, then $NaBH_4$ (0.66 g) was added, followed by the addition of glacial acetic acid (6 ml). After 15 minutes, $NaBH_4$ (1.08 g) was added, and the reaction was stirred at room temperature for 15 hours. An additional quantity of $NaBH_4$ (1.66 g) was then added and the reaction was stirred at room temperature for 3 hours before it was quenched with HCl (1M, 200 ml). The mixture was then extracted with ethyl acetate (2×150 ml). The organic layers were combined, washed with saturated NaCl solution (100 ml), dried over $Na_2SO_4$, filtered, and the solvent removed under reduced pressure to afford a yellow solid (9.03 g) having ESMS Negative ion mode $M\text{-}H^+$ Calculated 224 Found 224.

Example 6

Synthesis of $N^{\beta\text{-}Boc}$-2-(4-Phenyl-3-thiosemicarbazidyl) acetic acid 2-(4-Phenyl-3-thiosemicarbazidyl)acetic acid (8.93 g, 37.9 mmol, 100 mol %) and $(BOC)_2O$ (9.10 g) were dissolved in dioxane (100 ml). Sodium carbonate (1M, 50 ml) and water (50 ml) were added and the mixture was stirred at room temperature for 5 hours. Sodium hydroxide (1M, 40 ml) and an additional quantity of $(BOC)_2O$ (6.21 g) were added and the reaction was stirred overnight at room temperature. The reaction was quenched with citric acid (1M) and extracted with ethyl acetate (2×100 ml). The organic layers were combined, washed with saturated NaCl (50 ml), dried over $Na_2SO_4$, and filtered. The filtrate was concentrated under reduced pressure to afford a gummy solid (19 g). The crude solid was suspended in ether and a white solid was collected by filtration. The solid was washed with ether (100 ml) to obtain the desired product (3.17 g) having ESMS $MH^+$ calculated 326, found 326.

Example 7

Synthesis of $N^a$-(triphenylmethylsulfenyl)-$N^b$-(Boc) azaglycine $^t$-Butylcarbazate was condensed with glyoxylic acid monohydrate in methanol. This crude hydrazone was then reduced by catalytic hydrogenation over 10% Pd/C. This product was then mixed with dioxane and base and a dioxane solution of triphenylmethanesulfenylchloride was added dropwise. The desired $N^a$-(triphenylmethylsulfenyl)-$N^b$-(Boc)azaglycine (25 g) was obtained on work-up.

Example 8

Solid Phase Peptide Synthesis of Peptides Using Alloc and Fmoc Protecting Groups Solid phase peptide synthesis was carried out on a 0.050 mmol scale using an Advanced ChemTech model 348 peptide synthesizer modified to operate under nitrogen pressure in the same manner as the model 396. The 9-fluorenylmethyloxycarbonyl (Fmoc) group was employed for nitrogen protection and diisopropylcarbodiimide (DIC)/hydroxybenzotriazole (HOBT) were used to activate the carboxyl groups for coupling. A variety of resins were used such as Rink, Pal, and TentaGel S RAM for C-terminal amides and Wang, 2-chlorotrityl, or TentaGel S PHB for C-terminal acids. The alloc groups were cleaved on the machine in the manual mode by washing the resin bound peptide with dichloromethane (3×2 ml portions) and then mixing the resin with a solution (2 ml) containing tetrakistriphenylphosphine palladium [0] (10 mg), and acetic acid (0.1 ml). Tributyltinhydride (0.3 ml) was then added and the mixture was vortexed for one hour. The reaction cell was then emptied, the resin was washed with dichloromethane (3×2 ml) and standard Fmoc synthesis was then resumed. The peptides were cleaved from the resin with a solution of trifluoroacetic acid (TFA), anisole and ethane dithiol for 1 to 3 hours in the ratio 23:3:1. The crude cleavage mixture was then poured into ether to precipitate the crude peptide which was then purified by reverse phase HPLC using a Waters Delta Pak, Prep Pak C-18 cartridge system eluted with an appropriate gradient of TFA (0.1%) in water and/or TFA (0.1%) in acetonitrile (90%) and water (10%). The fractions containing the desired purified peptides were collected and the volatile solvents were removed under reduced pressure to obtain the aqueous solutions of the peptides which were then lyophilized. Samples of the lyophilized products were then sent for electrospray (ESMS) or fast atom bombardment (FABMS) to confirm that the observed mass of the products matched the calculated mass of the desired peptide.

The table below shows some of the peptide sequences (SEQ ID NOS: 1,3–17) Respectively synthesized by the methods described above.

| Peptide | HPLC[a] | MW[b] |
|---|---|---|
| <GHWSYGLRPG—$NH_2$ | 6.1 | 1183 |
| <GHYSLEWKPG—$NH_2$ | 6.2 | 1227 |
| <GHWSYK(MaGC)LRPG—$NH_2$ | 6.3 | 1488 |
| <GHYSLK(MaGC)WKPG—$NH_2$ | 6.3 | 1460 |
| <GHWSYK(Ms-azoGC)LRPG—$NH_2$ | 6.1 | 1503 |
| <GHYSLK(PtacGC)WKPG—$NH_2$ | 6.9 | 1536 |
| $AcNal_dCps_dW_dSRK_d$(MaGC)$LRPA_d$—$NH_2$ | 8.2 | 1668 |
| <GHYSYLK(PtacGDsp)WKPG—$NH_2$ | 6.6 | 1519 |
| <GHYSLK(azaGGC)WKPG—$NH_2$ | 6.5 | 1474 |

-continued

| | | |
|---|---|---|
| $Nal_dCps_dW_dSRK_d$(PtacGC)WKPG—$NH_2$ | 8.1 | 1701 |
| <GHWSYK$_d$(MaGC)LRPG—$NH_2$ | 6.3 | 1488 |
| $AcNal_dCps_dW_dSRK_d$(AzaGPC)$LRPA_d$—$NH_2$ | | |
| $AcNal_dCps_dW_dSRK_d$(MaPC)$LRPA_d$—$NH_2$ | | |
| $AcNal_dCps_dW_dSRK_d$(PtacGC)$LRPA_d$—$NH_2$ | | |
| <GHWSYK(iDGDep)LRPG—$NH_2$ | | |
| <GHWSYK(iECG)LRPG—$NH_2$ | | |

[a]HPLC Method [retention time in minutes] Solvent A is 0.1% trifluoroacetic acid in water, Solvent B is 0.1% trifluoroacetic acid in 90:10 acetonitrile/water Solvent flow rate is 3 ml/min for 10 min then 5 ml/min for 5 min Gradient is 0 to 100% B over 10 min then 100% B for 5 min
[b]Electrospray mass spectrum values ($MH^+$)

Abbreviations used in Table:

| | |
|---|---|
| <G: | pyroglutamic acid |
| PtacG: | 2-(4-phenyl-3-thiosemicarbazidyl)acetic acid or $PhNHCSNHNHCH_2CO2_2H$ |
| Ma: | mercaptoacetic acid |
| azaG: | azaglycine or $H_2NNHCH_2CO_2H$ |
| Dap: | 2,3-diaminoproprionic acid |
| Nal: | 2-naphthylalanine |
| Cpa: | 4-chlorophenylalanine |
| $K_d$: | the subscript d denotes that the D isomer was used |
| K(MaGC): | the parentheses denote that enclosed amino acids are attached to the e amine of lysine and the first amino acid attached is C followed by G and ending in Ma |
| iD: | isoaspartic acid |
| iE: | isoglutamic acid |

Example 9

Radiolabeling with TC-99m

A Glucoscan (DuPont) vial was reconstituted with 2.18 mCi of $NaTcO_4$ in 1 ml saline to form the Tc-99m-gluceptate complex. <GHWSYK(MaGC)LRPG amide (SEQ ID NO:4) (IMP3) was prepared as above. Tc-99m-IMP3 was prepared by mixing 360 $\mu$l (874 uCi) of Tc-99m-gluceptate with 640 $\mu$l of peptide in saline. The initially formed precipitate disappeared upon heating for 15 min at 75° C. An instant TLC(ITLC) strip developed in $H_2O$:EtOH:$NH_4OH$ mixture (5:2:1) showed 6.2% of the activity at the origin as colloids. HPLC showed 100% of the activity bound to the peptide with a RT of 6.95 min, whereas the unlabeled peptide eluted at 6.4 min under the same HPLC conditions (reversed phase C-18 column, gradient of 0–100% B in 10 min at a flow rate of 3 ml/min, where A is 0.1% TFA in $H_2O$ and B is 90% $CH_3CN$, 0.1% TFA). Recovery from the HPLC column was 85% of the injected activity.

IMP3 was formulated and lyophilized for Tc-99m labeling in the amounts shown below:

| | IMP3 ($\mu$g) | Sn ($\mu$g) | αDG/Sn |
|---|---|---|---|
| 1. | 250 | 23 | 14 |
| 2. | 100 | 23 | 14 |
| 3. | 250 | 15 | 14 |

The lyophilized vials were reconstituted with ~900 $\mu$uCi of $NaTcO_4$ in saline. Cloudiness was observed in all the vials. The vials were heated for 15 min at 75° C., but turbidity persisted. ITLC analysis for colloids showed 14, 21 and 9% colloids at the origin for vials 1, 2, and 3, respectively.

In order to prevent the precipitation during Tc-99m labeling. α-D-glucoheptonate(aDG) and tartrate ratios to Sn(II) were varied in the lyophilized vials. The following vials were formulated and lyophilized (250 $\mu$g of IMP3 with 25 $\mu$g Sn(II)) with tartrate and αDG ratios as shown below. The vials were reconstituted with ~500 $\mu$Ci of $NaTcO_4$ in 1 ml saline. Observatoins are indicated in the observation column. ITLC strips were developed after 15 min at room temperature following heating at 75° C. for 15 min.

| | tartrate/Sn | pH | Observation | colloid, RT | colloid, 75° C. |
|---|---|---|---|---|---|
| 1. | 50 | 5.3 | ppt | | |
| 2. | 100 | 5.3 | ppt | | |
| 3. | 500 | 5.3 | ppt clears upon mixing | 17% | 2.4% |
| | αDG/Sn | pH | Observation | colloid, RT | colloid, 75° C. |
| 4. | 25 | 5.3 | ppt | | |
| 5. | 50 | 5.3 | ppt | | |
| 6. | 100 | 5.3 | turbid | | |
| 7. | 500 | 5.3 | slight turbidity | 25% | 3.5% |
| 8. | 1000 | 5.3 | clear | 3.3% | 3.1% |

The protocol above was repeated for vials 3, 7 and 8 and colloids were determined to be 5.3, 3.8, and 4.6%, respectively after heating 15 min at 75° C. A single broad peak was observed on a reversed HPLC column at a RT of 7 min. Results from labeling other peptides with technetium-99 are shown in the table below: (SEQ ID NO:4–8, 12, 9–11 respectively)

| Peptide | HPLC retention time (UV) | HPLC retention time (radiometric) | Electrospray mass spectrum |
|---|---|---|---|
| <GHWSYK(MaGC)LRPG.amide | 6.35 | 6.90 | 1488 |
| <GHYSLK(MaGC)WKPG.amide | 6.48 | 7.07 | 1460 |
| <GHWSYK(Ma-azaGC)LRPG.amide | 6.55 | 7.02 | 1503 |
| <GHYSLK(Ptac-GC)WKPG amide | 7.05 | 7.60 | 1536 |
| $AcNal_dCps_dW_dSRK_d(MaGC)LRPA_d—NH_2$ | | 8.50 (27%), 9.00 (68%) | |
| $<GHWSYK_d(MaGC)LRPG—NH_2$ | 6.83 (95%) | | |
| <GHYSYLK(PtacGDap)WKPG—$NH_2$ | 7.06 (96%) | | |
| <GHYSLK(azaGGC)WKPG—$NH_2$ | 6.60 (100%) | | |
| $Nal_dCpa_dW_dSRK_dWKPG—NH_2$ | 8.43 (97%) | | |

Abbreviations used in the table are the same as in Example 8 supra.

Example 10

Radiolabeling of IMP-3 Re-188

IMP3, (<GHWSYK(MaGC)LRPG amide) (SEQ ID NO:4) was synthesized as above. IMP 3 has a retention time of 6.4 min on a reversed phase C-18 column using a gradient of 0–100% B in 10 min at a flow rate of 3 ml/min where A is 0.1% TFA in $H_2O$ and B is 90% $CH_3CN$, 0.1% TFA.

IMP3 was formulated in 1 mg and 250 μg amounts with 450 μg Sn(II) and α-D-glucoheptonate at a ratio of 1:17.5, and lyophilized. The lyophilized vials of IMP3 (1 mg and 250 μg) were reconstituted with 617 and 578 μCi of $NaReO_4$ in saline. The vials were heated for 15 min at 75° C. HPLC analysis under the conditions described above showed single peaks at RT of 7.0 min for both vials. The effluent was collected and counted on a γ-counter. For the 1 mg vial, the recovery of activity was 88% whereas the recovery was 77% for the 250 μg vial. Colloid analyses on an ITLC strip developed in $H_2O$:EtOH:$NH_4OH$(5:2:1) showed 1.4 and 1.2% of the activity at the origin for 1 mg and 250 μg vials, respectively.

Re-188 labeling at room temperature did not proceed as well as at 75° C. At room temperature, only a few percent of the activity (<5%) was incorporated into the peptide and the rest of the activity eluted in the void volume (1.2 min).

Example 11

In vitro Receptor Binding Assays

The human breast adenocarcinoma cell lines MCF-7, SK-BR-3, and MDA-MB-231 were purchased from the American Type Culture Collection, Rockville, Md. Cells were grown in DMEM supplemented with 5% fetal bovine serum. 5% defined equine serum, penicillin (100 U/ml), streptomycin (100 μg/ml), and L-glutamine (2 mM). The cells were routinely passaged after detachment with trypsin and 0.2% EDTA.

Specificity of the unlabeled peptides is determined by competitive cell binding assay. Target cells are washed with fresh medium, and adjusted to $5\times10^5$ cell/ml. 100 μl of the cell suspension (100 μl) is added per well to a 96-well microtiter plate. The cells are allowed to attach and are then treated with different concentrations of the peptides in the presence of $^{125}$I-LHRH (Amersham Life Science, Arlington Heights, Ill. 2,000 Ci/mmol). Following a 2 h incubation at room temperature with shaking, the cells are washed twice and the radioactivity associated with the cells is counted and the concentration of the peptides that cause 50% inhibition on the binding of the labeled LH-RH is compared.

To determine receptor binding constants, serial dilutions of radiolabeled LHRH are incubated with $5\times10^5$ cells in a 96-well plate. All assay are performed in triplicates both with or without a high concentration of unlabeled LHRH to allow determination of specifically bound peptide. After a 2 h incubation at room temperature, the cells are washed and counted. The equilibrium association constant, $K_a$, and the total number of receptor sites per cell are determined by Scatchard analysis.

Example 12

Biodistribution Studies

MCF-7 tumor cells are injected into estrogen-dosed nude mice, and a tumor is allowed to develop. Carrier-free $^{125}$I-LHRH (~2000 Ci/mmol, Amersham Life Science) is injected into the mice and the mice are sacrificed at 5 min, 30 min, 1 hr, and 3 hr (3 animals per time point). The major organs, as well as the blood, and the tumor are removed, weighed, and counted to determine the percent injected dose per gram (% ID/g) in each organ.

Increasing amounts of unlabeled LHRH in 5 doses (from 0 to 0.1 mg) are then mixed with the $^{125}$I-LHRH and injected into the tumor-bearing nude mice (3 animals/dose) which are then sacrificed at time points determined from the previous experiment. This then allows determination of the LHRH receptor capacity in the nude mouse model.

Tc-99m labeled peptides that demonstrate superior in vitro receptor affinity as determined above are then screened in the MCF-7 nude mouse model. The Tc-99m labeled peptide is purified by HPLC to obtain the peptide carrier free metal complex for these studies if the LHRH receptor capacity is too low to tolerate the presence of excess peptide. The biodistribution of the Tc-99m label (3 animals per peptide) is monitored on a gamma camera equipped with a pinhole collimator. In the initial screen the animals are sacrificed after 4 hr and the biodistribution determined as described above. In subsequent experiments those Tc-99m labeled peptides that provide clear tumor images in the experiment described above are screened in additional animals (3 per time point), sacrificing at 15 min, 1 hr and 3 hr. The peptides are also tested in a blocking assay using LHRH. Coinjection of LHRH decreases tumor uptake of the radiolabeled peptides in a dose-dependent manner, demonstrating that the in vivo tumor uptake is specific.

The invention has been disclosed broadly and illustrated in reference to representative embodiments described above. Those skilled in the art will recognize that various modifications can be made to the present invention without departing from the spirit and scope thereof.

[The invention has been disclosed broadly and illustrated in reference to representative embodiments described above. Those skilled in the art will recognize that various modifications can be made to the present invention without departing from the spirit and scope thereof.]

SEQUENCE LISTING

```
(1) GENERAL INFORMATION:

   (iii) NUMBER OF SEQUENCES: 17


(2) INFORMATION FOR SEQ ID NO: 1:

     (i) SEQUENCE CHARACTERISTICS:
          (A) LENGTH: 10 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = pyroglutamic acid."

    (xi) SEQUENCE DESCRIPTION: SEQ ID NO: 1:

Xaa His Trp Ser Tyr Gly Leu Arg Pro Gly
1               5                   10


(2) INFORMATION FOR SEQ ID NO: 2:

     (i) SEQUENCE CHARACTERISTICS:
          (A) LENGTH: 10 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = pyroglutamic acid or
               D-acetylnap hthylalanine."

    (ix) FEATURE:
          (A) NAME/KEY: Modified-si te
          (B) LOCATION: 2
          (D) OTHER INFORMATION: /product= "OTHER"
               /note= "The Xaa at position 2 = His or
               D-4-chlorop henylalanine."

    (ix) FEATURE:
          (A) NAME/KEY: Modified-si te
          (B) LOCATION: 3
          (D) OTHER INFORMATION: /product= "OTHER"
               /note= "The Xaa at position 3 = D- or L-Trp o r Tyr."

    (ix) FEATURE:
          (A) NAME/KEY: Modified-si te
          (B) LOCATION: 5
          (D) OTHER INFORMATION: /product= "OTHER"
               /note= "The Xaa at position 5 = Tyr or Leu or  Arg."

    (ix) FEATURE:
```

-continued

```
          (A) NAME/KEY: Modified-si te
          (B) LOCATION: 6
          (D) OTHER INFORMATION: /product= "OTHER"
               /note= "The Xaa at position 6 = a D- or L- amino acid
               derivative capable of chelating a radiometal."

    (ix) FEATURE:
          (A) NAME/KEY: Modified-si te
          (B) LOCATION: 7
          (D) OTHER INFORMATION: /product= "OTHER"
               /note= "The Xaa at position 7 = Leu or Trp."

    (ix) FEATURE:
          (A) NAME/KEY: Modified-si te
          (B) LOCATION: 8
          (D) OTHER INFORMATION: /product= "OTHER"
               /note= "The Xaa at position 8 = Arg or Lys."

    (ix) FEATURE:
          (A) NAME/KEY: Modified-si te
          (B) LOCATION: 10
          (D) OTHER INFORMATION: /product= "OTHER"
               /note= "The Xaa at position 10 = glycine amide o r
               D-alanine amide."

    (xi) SEQUENCE DESCRIPTION: SEQ ID NO: 2:

Xaa Xaa Xaa Ser Xaa Xaa Xaa Xaa Pro Xaa
1               5                   10


(2) INFORMATION FOR SEQ ID NO: 3:

     (i) SEQUENCE CHARACTERISTICS:
          (A) LENGTH: 10 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = polyglutamic acid."

    (xi) SEQUENCE DESCRIPTION: SEQ ID NO: 3:

Xaa His Tyr Ser Leu Glu Trp Lys Pro Gly
1               5                   10


(2) INFORMATION FOR SEQ ID NO: 4:

     (i) SEQUENCE CHARACTERISTICS:
          (A) LENGTH: 11 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = polyglutamic acid."

    (ix) FEATURE:
          (A) NAME/KEY: Modified-si te
          (B) LOCATION: 7
          (D) OTHER INFORMATION: /product= "OTHER"
               /note= "The Xaa at position 7 = (Cys attached to  Gly
               attached to mercaptoacetic acid) attached to the e amine
               of Lys."

    (xi) SEQUENCE DESCRIPTION: SEQ ID NO: 4:

Xaa His Trp Ser Tyr Lys Xaa Leu Arg Pro G ly
1               5                   10
```

-continued (2) INFORMATION FOR SEQ ID NO: 5:

(i) SEQUENCE CHARACTERISTICS:
(A) LENGTH: 11 amino acids
(B) TYPE: amino acid
(C) STRANDEDNESS: single
(D) TOPOLOGY: linear (ix) FEATURE:
(A) NAME/KEY: Modified-si te
(B) LOCATION: 1
(D) OTHER INFORMATION: /product= "OTHER"
/note= "The Xaa at position 1 = polyglutamic acid."

(ix) FEATURE:
(A) NAME/KEY: Modified-si te
(B) LOCATION: 7
(D) OTHER INFORMATION: /product= "OTHER"
/note= "The Xaa at position 7 = (Cys attached to Gly attached to mercaptoacetic acid) attached to the e amine of Lys."

(xi) SEQUENCE DESCRIPTION: SEQ ID NO: 5:

Xaa His Tyr Ser Leu Lys Xaa Trp Lys Pro G ly
1 5 10

(2) INFORMATION FOR SEQ ID NO: 6:

(i) SEQUENCE CHARACTERISTICS:
(A) LENGTH: 12 amino acids
(B) TYPE: amino acid
(C) STRANDEDNESS: single
(D) TOPOLOGY: linear (ix) FEATURE:
(A) NAME/KEY: Modified-si te
(B) LOCATION: 1
(D) OTHER INFORMATION: /product= "OTHER"
/note= "The Xaa at position 1 = polyglutamic acid."

(ix) FEATURE:
(A) NAME/KEY: Modified-si te
(B) LOCATION: 7
(D) OTHER INFORMATION: /product= "OTHER"
/note= "The Xaa at position 7 = mercaptoacetic acid ."

(ix) FEATURE:
(A) NAME/KEY: Modified-si te
(B) LOCATION: 8
(D) OTHER INFORMATION: /product= "OTHER"
/note= "The Xaa at position 8 = azaglycine or H2NNHCH2CO2 H."

(xi) SEQUENCE DESCRIPTION: SEQ ID NO: 6:

Xaa His Trp Ser Tyr Lys Xaa Xaa Leu Arg P ro Gly
1 5 10

(2) INFORMATION FOR SEQ ID NO: 7:

(i) SEQUENCE CHARACTERISTICS:
(A) LENGTH: 11 amino acids
(B) TYPE: amino acid
(C) STRANDEDNESS: single
(D) TOPOLOGY: linear (ix) FEATURE:
(A) NAME/KEY: Modified-si te
(B) LOCATION: 1
(D) OTHER INFORMATION: /product= "OTHER"
/note= "The Xaa at position 1 = polyglutamic acid."

(ix) FEATURE:
(A) NAME/KEY: Modified-si te
(B) LOCATION: 7
(D) OTHER INFORMATION: /product= "OTHER"

-continued

```
                /note= "The Xaa at position 7 =
                2-(4-phenyl -3-thiosemicarbazidyl) acetic acid or
                PhNHCSNHNHC H2CO2H."

    (xi) SEQUENCE DESCRIPTION: SEQ ID NO: 7:

Xaa His Tyr Ser Leu Lys Xaa Trp Lys Pro G ly
1               5                   10


(2) INFORMATION FOR SEQ ID NO: 8:

     (i) SEQUENCE CHARACTERISTICS:
          (A) LENGTH: 12 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = acetyl group."

    (ix) FEATURE:
          (A) NAME/KEY: Modified-si te
          (B) LOCATION: 2
          (D) OTHER INFORMATION: /product= "OTHER"
               /note= "The Xaa at position 2 = the D isomer of
               2-naphthyla lanine."

    (ix) FEATURE:
          (A) NAME/KEY: Modified-si te
          (B) LOCATION: 3
          (D) OTHER INFORMATION: /product= "OTHER"
               /note= "The Xaa at position 3 = the D isomer of
               4-chlorophe nylalanine."

    (ix) FEATURE:
          (A) NAME/KEY: Modified-si te
          (B) LOCATION: 4
          (D) OTHER INFORMATION: /product= "OTHER"
               /note= "The Xaa at position 4 = the D isomer of Trp."

    (ix) FEATURE:
          (A) NAME/KEY: Modified-si te
          (B) LOCATION: 7
          (D) OTHER INFORMATION: /product= "OTHER"
               /note= "The Xaa at position 7 = the D isomer of Lys."

    (ix) FEATURE:
          (A) NAME/KEY: Modified-si te
          (B) LOCATION: 8
          (D) OTHER INFORMATION: /product= "OTHER"
               /note= "The Xaa at position 8 = (Cys attached to  Gly
               attached to mercaptoacetic acid) attached to the e amine
               of Lys."

    (ix) FEATURE:
          (A) NAME/KEY: Modified-si te
          (B) LOCATION: 12
          (D) OTHER INFORMATION: /product= "OTHER"
               /note= "The Xaa at position 12 = the D isomer of Ala."

    (xi) SEQUENCE DESCRIPTION: SEQ ID NO: 8:

Xaa Xaa Xaa Xaa Ser Arg Xaa Xaa Leu Arg P ro Xaa
1               5                   10


(2) INFORMATION FOR SEQ ID NO: 9:

     (i) SEQUENCE CHARACTERISTICS:
          (A) LENGTH: 13 amino acids
          (B) TYPE: amino acid
          (C) STRANDEDNESS: single
          (D) TOPOLOGY: linear

    (ix) FEATURE:
```

-continued

```
          (A) NAME/KEY: Modified-si te
          (B) LOCATION: 1
          (D) OTHER INFORMATION: /product= "OTHER"
               /note= "The Xaa at position 1 = polyglutamic acid."

    (ix) FEATURE:
          (A) NAME/KEY: Modified-si te
          (B) LOCATION: 8
          (D) OTHER INFORMATION: /product= "OTHER"
               /note= "The Xaa at position 8 =
               2-(4-phenyl -3-thiosemicarbazidyl) acetic acid or
               PhNHCSNHNHC H2CO2H."

    (ix) FEATURE:
          (A) NAME/KEY: Modified-si te
          (B) LOCATION: 9
          (D) OTHER INFORMATION: /product= "OTHER"
               /note= "The Xaa at position 9 = 2,3-diaminoproprionic
               acid."

    (xi) SEQUENCE DESCRIPTION: SEQ ID NO: 9:

Xaa His Tyr Ser Tyr Leu Lys Xaa Xaa Trp L ys Pro Gly
1               5                   10


(2) INFORMATION FOR SEQ ID NO: 10:

     (i) SEQUENCE CHARACTERISTICS:
          (A) LENGTH: 11 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = polyglutamic acid."

    (ix) FEATURE:
          (A) NAME/KEY: Modified-si te
          (B) LOCATION: 7
          (D) OTHER INFORMATION: /product= "OTHER"
               /note= "The Xaa at position 7 = (Cys attached to  Gly
               attached to azaglycine or H2NNHCH2CO2H) attached to the
               e amine of Lys."

    (xi) SEQUENCE DESCRIPTION: SEQ ID NO: 10:

Xaa His Tyr Ser Leu Lys Xaa Trp Lys Pro G ly
1               5                   10


(2) INFORMATION FOR SEQ ID NO: 11:

     (i) SEQUENCE CHARACTERISTICS:
          (A) LENGTH: 11 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = the D isomer of
               2-naphthyla lanine."

    (ix) FEATURE:
          (A) NAME/KEY: Modified-si te
          (B) LOCATION: 2
          (D) OTHER INFORMATION: /product= "OTHER"
               /note= "The Xaa at position 2 = 4-chlorophenylalanine. "

    (ix) FEATURE:
          (A) NAME/KEY: Modified-si te
          (B) LOCATION: 3
          (D) OTHER INFORMATION: /product= "OTHER"
```

-continued

```
                /note= "The Xaa at position 3 = the D isomer of Trp."

    (ix) FEATURE:
          (A) NAME/KEY: Modified-si te
          (B) LOCATION: 6
          (D) OTHER INFORMATION: /product= "OTHER"
               /note= "The Xaa at position 6 = the D isomer of Lys."

    (ix) FEATURE:
          (A) NAME/KEY: Modified-si te
          (B) LOCATION: 7
          (D) OTHER INFORMATION: /product= "OTHER"
               /note= "The Xaa at position 7 = (Cys attached to
               2-(4-phenyl -3-thiosemicarbazidyl) acetic acid or
               PhNHCSNHNHC H2CO2H) attached to the e amine of Lys."

    (xi) SEQUENCE DESCRIPTION: SEQ ID NO: 11:

Xaa Xaa Xaa Ser Arg Xaa Xaa Trp Lys Pro G ly
1               5                   10


(2) INFORMATION FOR SEQ ID NO: 12:

     (i) SEQUENCE CHARACTERISTICS:
          (A) LENGTH: 11 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = polyglutamic acid."

    (ix) FEATURE:
          (A) NAME/KEY: Modified-si te
          (B) LOCATION: 6
          (D) OTHER INFORMATION: /product= "OTHER"
               /note= "The Xaa at position 6 = the D isomer of Lys."

    (ix) FEATURE:
          (A) NAME/KEY: Modified-si te
          (B) LOCATION: 7
          (D) OTHER INFORMATION: /product= "OTHER"
               /note= "The Xaa at position 7 = (Cys attached to  Gly
               attached to mercaptoacetic acid) attached to the e amine
               of Lys."

    (xi) SEQUENCE DESCRIPTION: SEQ ID NO: 12:

Xaa His Trp Ser Tyr Xaa Xaa Leu Arg Pro G ly
1               5                   10


(2) INFORMATION FOR SEQ ID NO: 13:

     (i) SEQUENCE CHARACTERISTICS:
          (A) LENGTH: 12 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = an acetyl group. "

    (ix) FEATURE:
          (A) NAME/KEY: Modified-si te
          (B) LOCATION: 2
          (D) OTHER INFORMATION: /product= "OTHER"
               /note= "The Xaa at position 2 = the D isomer of
               2-naphthyla lanine."

    (ix) FEATURE:
          (A) NAME/KEY: Modified-si te
```

-continued

```
          (B) LOCATION: 3
          (D) OTHER INFORMATION: /product= "OTHER"
               /note= "The Xaa at position 3 = 4-chlorophenylalanine. "

    (ix) FEATURE:
          (A) NAME/KEY: Modified-si te
          (B) LOCATION: 4
          (D) OTHER INFORMATION: /product= "OTHER"
               /note= "The Xaa at position 4 = the D isomer of Trp."

    (ix) FEATURE:
          (A) NAME/KEY: Modified-si te
          (B) LOCATION: 7
          (D) OTHER INFORMATION: /product= "OTHER"
               /note= "The Xaa at position 7 = the D isomer of Lys."

    (ix) FEATURE:
          (A) NAME/KEY: Modified-si te
          (B) LOCATION: 8
          (D) OTHER INFORMATION: /product= "OTHER"
               /note= "The Xaa at position 8 = (Cys attached to  Phe
               attached to azaglycine or H2NNHCH2CO2H) attached to the
               e amine of Lys."

    (ix) FEATURE:
          (A) NAME/KEY: Modified-si te
          (B) LOCATION: 12
          (D) OTHER INFORMATION: /product= "OTHER"
               /note= "The Xaa at psition 12 = the D isomer of Ala."

    (xi) SEQUENCE DESCRIPTION: SEQ ID NO: 13:

Xaa Xaa Xaa Xaa Ser Arg Xaa Xaa Leu Arg P ro Xaa
1               5                   10


(2) INFORMATION FOR SEQ ID NO: 14:

     (i) SEQUENCE CHARACTERISTICS:
          (A) LENGTH: 12 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = an acetyl group. "

    (ix) FEATURE:
          (A) NAME/KEY: Modified-si te
          (B) LOCATION: 2
          (D) OTHER INFORMATION: /product= "OTHER"
               /note= "The Xaa at position 2 = the D isomer of
               2-naphthyla lanine."

    (ix) FEATURE:
          (A) NAME/KEY: Modified-si te
          (B) LOCATION: 3
          (D) OTHER INFORMATION: /product= "OTHER"
               /note= "The Xaa at position 3 = 4-chlorophenylalanine. "

    (ix) FEATURE:
          (A) NAME/KEY: Modified-si te
          (B) LOCATION: 4
          (D) OTHER INFORMATION: /product= "OTHER"
               /note= "The Xaa at posotion 4 = the D isomer of Trp."

    (ix) FEATURE:
          (A) NAME/KEY: Modified-si te
          (B) LOCATION: 7
          (D) OTHER INFORMATION: /product= "OTHER"
               /note= "The Xaa at position 7 = the D isomer of Lys."

    (ix) FEATURE:
          (A) NAME/KEY: Modified-si te
          (B) LOCATION: 8
          (D) OTHER INFORMATION: /product= "OTHER"
```

-continued

```
                /note= "The Xaa at position 8 = (Cys attached to  Phe
                attached to mercaptoacetic acid) attached to the e amine
                of Lys."

    (ix) FEATURE:
          (A) NAME/KEY: Modified-si te
          (B) LOCATION: 12
          (D) OTHER INFORMATION: /product= "OTHER"
               /note= "The Xaa at position 12 = the D isomer of Ala."

    (xi) SEQUENCE DESCRIPTION: SEQ ID NO: 14:

Xaa Xaa Xaa Xaa Ser Arg Xaa Xaa Leu Arg P ro Xaa
1               5                   10


(2) INFORMATION FOR SEQ ID NO: 15:

     (i) SEQUENCE CHARACTERISTICS:
          (A) LENGTH: 12 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = an acetyl group. "

    (ix) FEATURE:
          (A) NAME/KEY: Modified-si te
          (B) LOCATION: 2
          (D) OTHER INFORMATION: /product= "OTHER"
               /note= "The Xaa at position 2 = the D isomer of
               2-naphthyla lanine."

    (ix) FEATURE:
          (A) NAME/KEY: Modified-si te
          (B) LOCATION: 3
          (D) OTHER INFORMATION: /product= "OTHER"
               /note= "The Xaa at position 3 = the D isomer of
               4-chlorophe nylalanine."

    (ix) FEATURE:
          (A) NAME/KEY: Modified-si te
          (B) LOCATION: 4
          (D) OTHER INFORMATION: /product= "OTHER"
               /note= "The Xaa at position 4 = the D isomer of Trp."

    (ix) FEATURE:
          (A) NAME/KEY: Modified-si te
          (B) LOCATION: 7
          (D) OTHER INFORMATION: /product= "OTHER"
               /note= "The Xaa at position 7 = the D isomer of Lys."

    (ix) FEATURE:
          (A) NAME/KEY: Modified-si te
          (B) LOCATION: 8
          (D) OTHER INFORMATION: /product= "OTHER"
               /note= "The Xaa at position 8 = (Cys attached to
               2-(4-phenyl -3-thiosemicarbazidyl) acetyl acid or
               PhNHCSNHNHC H2CO2H) attached to the e amine of Lys."

    (ix) FEATURE:
          (A) NAME/KEY: Modified-si te
          (B) LOCATION: 12
          (D) OTHER INFORMATION: /product= "OTHER"
               /note= "The Xaa at position 12 = the D isomer of Ala."

    (xi) SEQUENCE DESCRIPTION: SEQ ID NO: 15:

Xaa Xaa Xaa Xaa Ser Arg Xaa Xaa Leu Arg P ro Xaa
1               5                   10


(2) INFORMATION FOR SEQ ID NO: 16:

     (i) SEQUENCE CHARACTERISTICS:
```

-continued

```
          (A) LENGTH: 12 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = polyglutamic acid."

    (ix) FEATURE:
          (A) NAME/KEY: Modified-si te
          (B) LOCATION: 7
          (D) OTHER INFORMATION: /product= "OTHER"
               /note= "The Xaa at position 7 = isoaspartic acid."

    (ix) FEATURE:
          (A) NAME/KEY: Modified-si te
          (B) LOCATION: 8
          (D) OTHER INFORMATION: /product= "OTHER"
               /note= "The Xaa at position 8 = 2,3-diaminoproprionic
               acid."

    (xi) SEQUENCE DESCRIPTION: SEQ ID NO: 16:

Xaa His Trp Ser Tyr Lys Xaa Xaa Leu Arg P ro Gly
1               5                   10


(2) INFORMATION FOR SEQ ID NO: 17:

     (i) SEQUENCE CHARACTERISTICS:
          (A) LENGTH: 11 amino acids
          (B) TYPE: amino acid
          (C) STRANDEDNESS: single
          (D) TOPOLOGY: linear

    (ix) FEATURE:
          (A) NAME/KEY: Modified-si te
          (B) LOCATION: 1
          (D) OTHER INFORMATION: /product= "OTHER"
               /note= "The Xaa at position 1 = polyglutamic acid."

    (ix) FEATURE:
          (A) NAME/KEY: Modified-si te
          (B) LOCATION: 7
          (D) OTHER INFORMATION: /product= "OTHER"
               /note= "The Xaa at position 7 = (Cys attached to  Gly
               attached to isoglutamic acid) attached to the e amine
               of Lys."

    (xi) SEQUENCE DESCRIPTION: SEQ ID NO: 17:

Xaa His Trp Ser Tyr Lys Glx Leu Arg Pro G ly
1               5                   10
```

What is claimed is:

1. A peptide comprising the amino acid sequence $X^1$-$X^2$-$X^3$-ser-$X^4$-$X^5$-$X^6$-$X^7$-pro-$X^8$-$NH_2$, wherein $X^1$ is pyroglutamic acid or D-acetylnaphthylalanine, $X^2$ is histidine or D-4-chlorophenylalanine, $X^3$ is D- or L-tryptophan or tyrosine, $X^4$ is tyrosine, leucine, or arginine, $X^6$ is leucine or tryptophan, $X^7$ is arginine or lysine, $X^8$-$NH_2$ is glycine amide or D-alanine amide, and wherein $X^5$ is an amino acid derivative capable of stably chelating technetium-99m, rhenium-186, or rhenium-188, and has the structure:

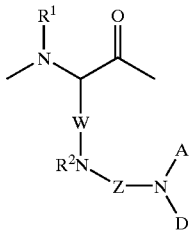

wherein $R^1$ is H, OH, peptide, a sugar, a targeting molecule, lower alkyl, substituted lower alkyl, or a protecting group that can be removed under the conditions of peptide synthesis;

$R^2$ is H, lower alkyl, or substituted lower alkyl; W is from 1–20 atoms long and is selected from the group consisting of cycloalkyl, aryl, or alkaryl groups, a substituted or unsubstituted alkylene chain, and a chain substituted with at least one heteroatom;

Z is an amino acid or a peptide containing 2–5 residues, or Z is $COCH_2$ or $COCH(CH_2SP^2)$, in which $P^2$ is H or a sulfur protecting group;

A and D are the same or different and each is selected from the group consisting of H, $COCH_2NR^3NR^4C(S)NHR^5$, $COCH_2NR^6NR^7C(S)NHR^8$, $COCH_2NR^9NR^{10}C(O)CH_2SP^2$, $CONR^{11}NR^{12}C(O)CH_2SP^2$, $NR^{13}C(S)NHR^{14}$, or $COCH_2NR^{15}COCH_2SP^2$;

$R^3$, $R^4$, $R^6$, $R^7$, $R^9$, $R^{10}$, $R^{11}$, $R^{12}$, $R^{13}$, and $R^{15}$ are the same or different, and each represents H, lower alkyl, or substituted lower alkyl; and $R^5$, $R^8$, and $R^{14}$ are the same or different and each is H, lower alkyl, substituted lower alkyl, aryl, or substituted aryl;

*or $X^5$ is selected from the group consisting of:*

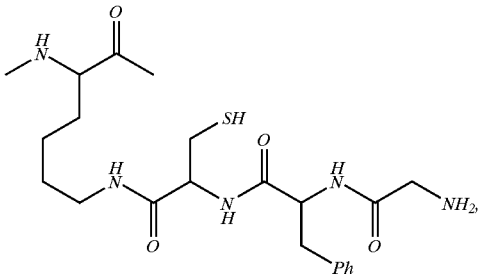

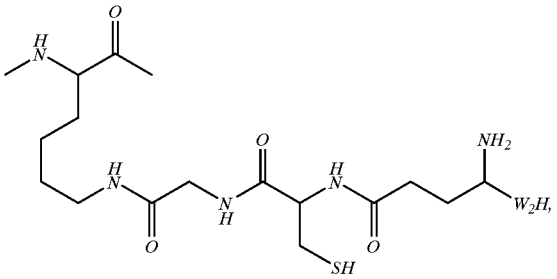

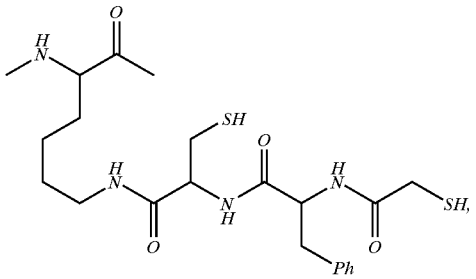

-continued

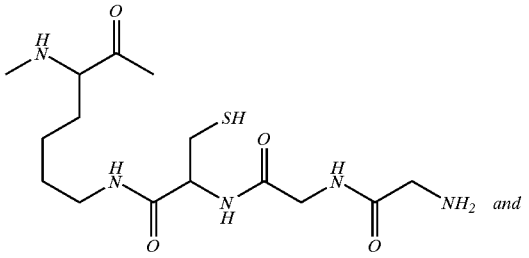

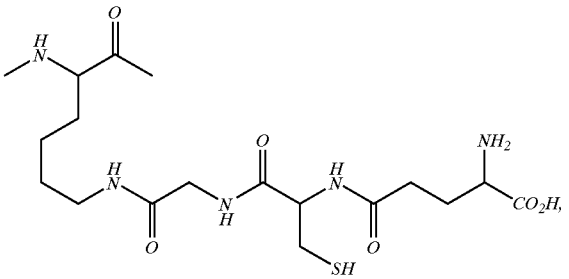

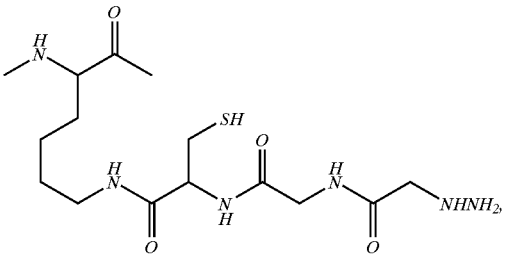

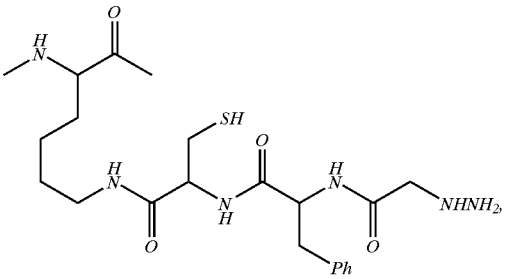

*wherein said amino acid sequence contains at least one thiol or thiocarbonyl group.*

2. A peptide according to claim 1, wherein $X^5$ is selected from the group consisting of:

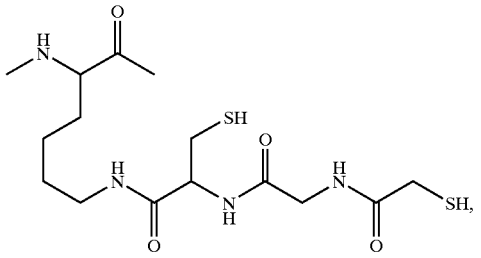

-continued

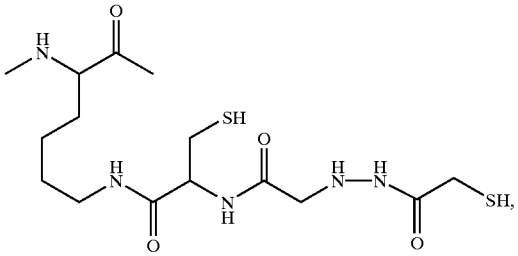

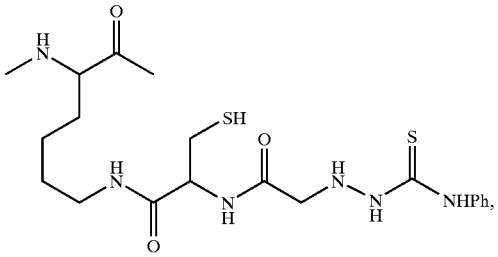

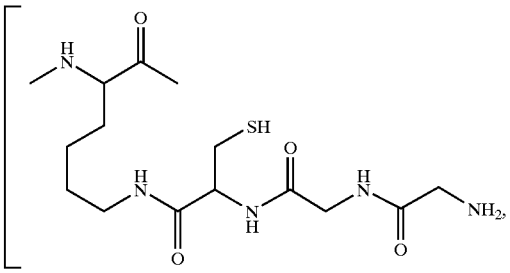

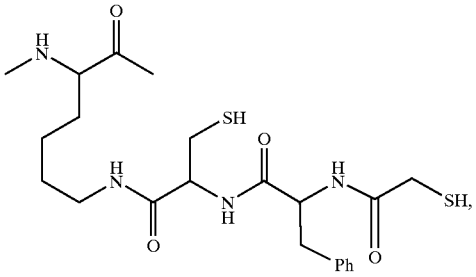

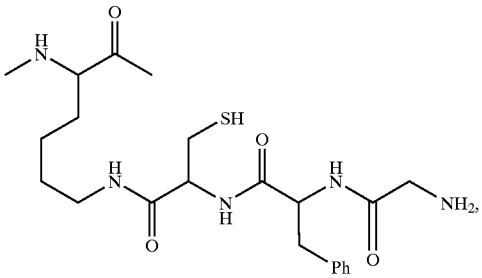

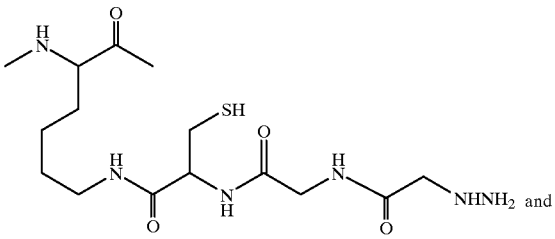

-continued

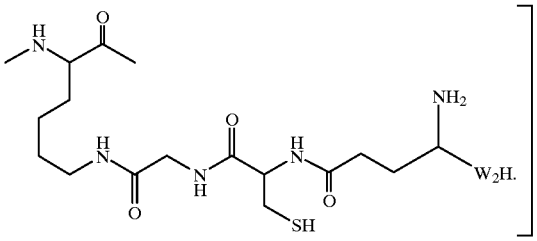

3. A peptide according to claim [2] *1*, wherein $X^1$ is pyro-glutamic acid, $X^2$ is histidine, and $X^8$ is glycine amide.

4. A peptide according to claim 3, wherein $X^3$ is tyrosine, $X^4$ is leucine, $X^6$ is tryptophan, and $X^7$ is lysine.

5. A peptide according to claim 4, wherein $X^5$ is

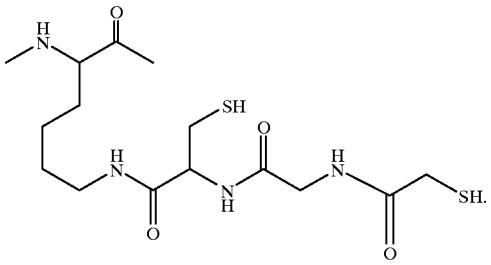

6. A peptide according to claim [5] *4*, wherein $X^5$ is

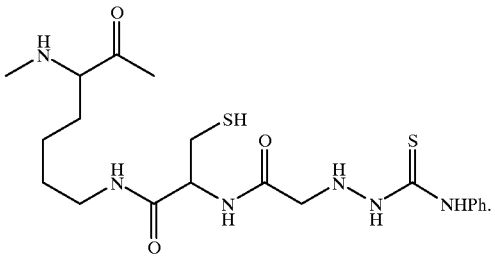

. A peptide according to claim 4, wherein $X^5$ is

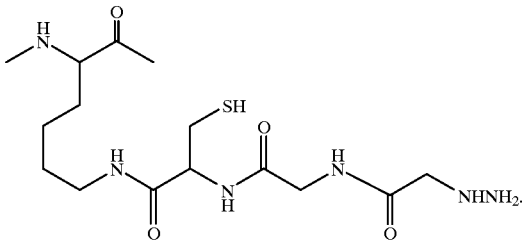

8. A peptide according to claim 3, wherein $X^3$ is tryptophan, $X^4$ is tyrosine, $X^6$ is leucine, and $X^7$ is arginine.

9. A peptide according to claim 8, wherein $X^5$ is

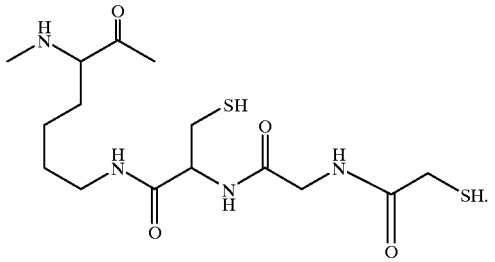

10. A peptide according to claim 8, wherein $X^5$ is

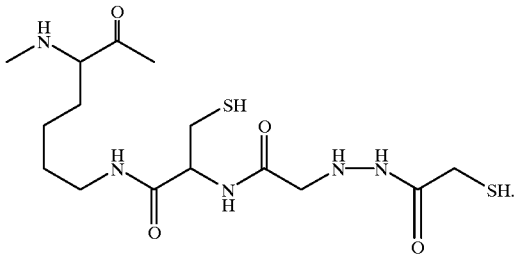

11. A peptide according to claim 8, wherein $X^5$ is

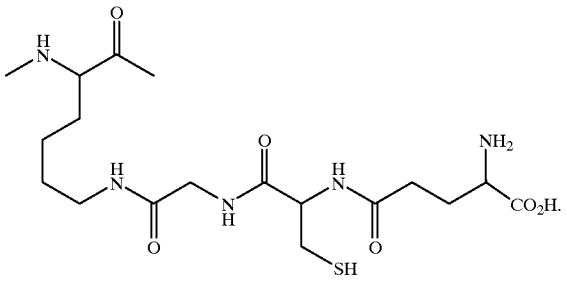

12. A peptide according to claim 2, wherein $X^1$ is D-acetylnaphthylalanine, $X^2$ is D-4-chlorophenylalanine, $X^3$ is D-tryptophan, $X^4$ is arginine, $X^6$ is leucine, $X^7$ is arginine, and $X^8$-$NH_2$ is D-alanine amide.

13. A peptide according to claim 12, wherein $X^5$ is

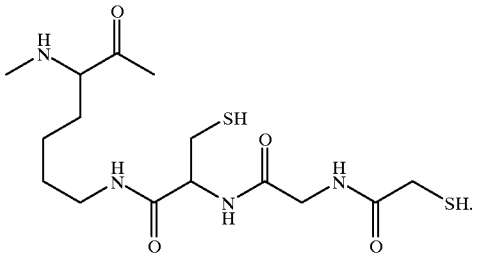

14. A peptide according to claim [12] *1*, wherein $X^5$ is

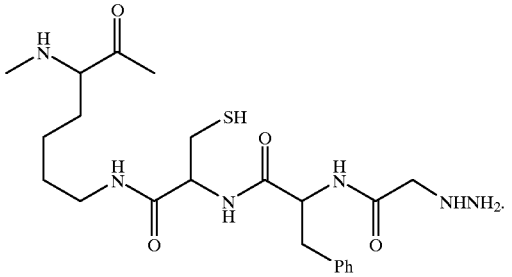

15. A peptide according to claim [12] *1*, wherein $X^5$ is

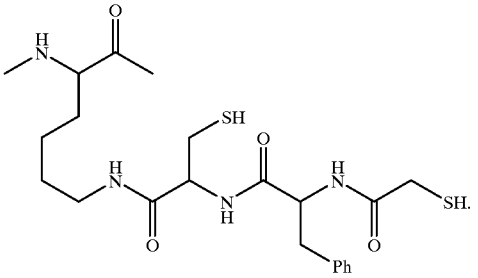

16. A peptide according to claim 12, wherein $X^5$ is

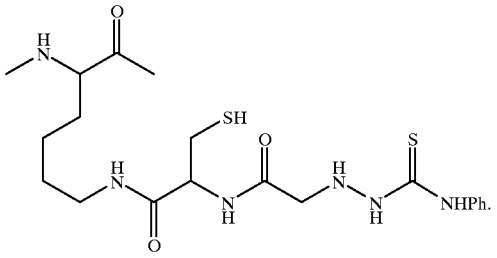

17. A peptide according to claim [2] *1*, wherein $X^1$ is D-acetylnaphthylalanine, $X^2$ is D-4-chlorophenylalanine, $X^3$ is D-tryptophan, $X^4$ is arginine, $X^6$ is tryptophan, $X^7$ is lysine, and $X^8$-$NH_2$ is glycine amide.

18. A method of preparing a metal-chelating composition, comprising contacting a solution of a peptide with stannous ions, wherein said peptide comprises the amino acid sequence $X^1$-$X^2$-$X^3$-ser-$X^4$-$X^5$-$X^6$-$X^7$-pro-$X^8$-$NH_2$, wherein $X^1$ is pyroglutamic acid or D-acetylnaphthylalanine, $X^2$ is histidine or D-4-chlorophenylalanine, $X^3$ is D- or L-tryptophan or tyrosine, $X^4$ is tyrosine, leucine, or arginine, $X^6$ is leucine or tryptophan, $X^7$ is arginine or lysine, $X^8$-$NH_2$ is glycine amide or D-alanine amide, $X^5$ is an amino acid derivative capable of stably chelating technetium-99m, rhenium-186, or rhenium-188, and has the structure:

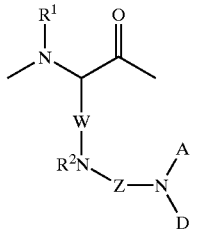

wherein $R^1$ is H, OH, a peptide, a sugar, a targeting molecule, lower alkyl, substituted lower alkyl, or a protecting group that can be removed under the conditions of peptide synthesis;

$R^2$ is H, lower alkyl, or substituted lower alkyl; W is from 1–20 atoms long and is selected from the group consisting of cycloalkyl, aryl, or alkaryl groups, a substituted or unsubstituted alkylene chain, and a chain substituted with at least one heteroatom;

Z is an amino acid or a peptide containing 2–5 residues, or Z is $COCH_2$ or $COCH(CH_2SP^2)$, in which $P^2$ is H or a sulfur protecting group;

A and D are the same or different, and each is selected from the group consisting of H, $COCH_2NR^3NR^4C(S)NHR^5$, $COCH_2NR^6NR^7C(S)NHR^8$, $COCH_2NR^9NR^{10}C(O)CH_2SP^2$, $CONR^{11}NR^{12}C(O)CH_2SP^2$, $NR^{13}C(S)NHR^{14}$, or $COCH_2NR^{15}COCH_2SP^2$;

$R^3$, $R^4$, $R^6$, $R^7$, $R^9$, $R^{10}$, $R^{11}$, $R^{12}$, $R^{13}$, and $R^{15}$ are the same or different, and each represents H, lower alkyl, or substituted lower alkyl; and $R^5$, $R^8$, and $R^{14}$ are the same or different and each is H, lower alkyl, substituted lower alkyl, aryl, or substituted aryl,

*or $X^5$ is selected from the group consisting of:*

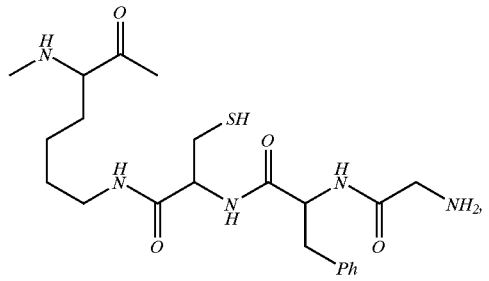

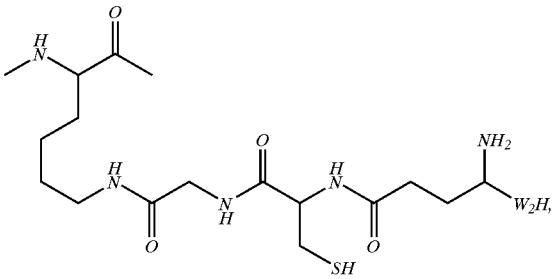

-continued

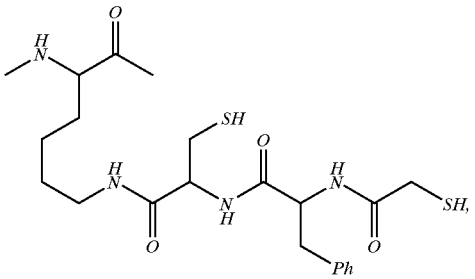

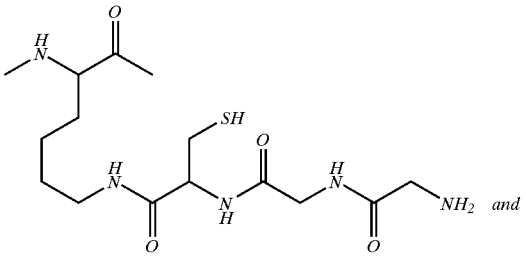

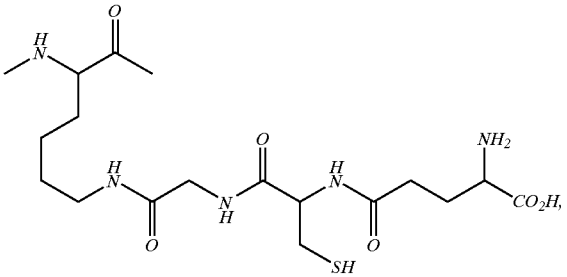

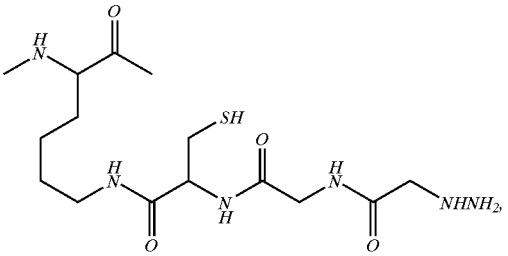

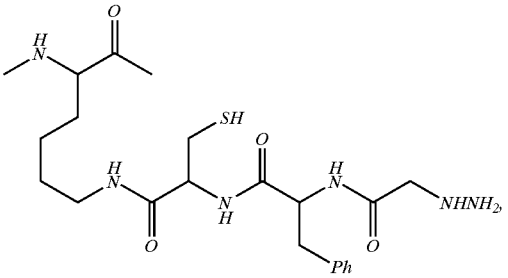

*wherein said amino acid sequence contains at least one thiol or thiocarbonyl group;* and then contacting said solution with $^{99m}$pertechnetate, $^{186}$perrhenate or $^{188}$perrhenate and recovering the radiolabeled peptide.

19. The method of claim 18, wherein said peptide specifically binds cells or tissues that express LHRH receptors.

20. The method of claim 18, wherein said radionuclide is selected from $^{188}$Re- or $^{186}$Re-perrhenate and $^{99}$Tc-pertechnetate.

21. A method of imaging a tumor, an infectious lesion, a myocardial infarction, a clot, artherosclerotic plaque, or a normal organ or tissue, comprising administering to a human patient a radiolabeled peptide that specifically binds to cells or tissues that express LHRH receptors, together with a pharmaceutically acceptable carrier, and, after a sufficient time for said radiolabeled peptide to localize and for non-target background to clear, the site or sites of accretion of said radiolabeled peptide detecting by an external imaging camera, wherein said radiolabeled peptide is prepared by contacting a solution of a peptide with stannous ions, wherein said peptide comprises the amino acid sequence $X^1$-$X^2$-$X^3$-ser-$X^4$-$X^5$-$X^6$-$X^7$-pro-$X^8$-$NH_2$, wherein $X^1$ is pyroglutamic acid or D-acetylnaphthylalanine, $X^2$ is histidine or D-4-chlorophenylalanine, $X^3$ is D- or L-tryptophan or tyrosine, $X^4$ is tyrosine, leucine, or arginine, $X^6$ is leucine or tryptophan, $X^7$ is arginine or lysine, and $X^8$-$NH_2$ is glycine amide or D-alanine amide, $X^5$ is an amino acid derivative capable of stably chelating technetium-99m, rhenium-186, or rhenium-188, and has the structure:

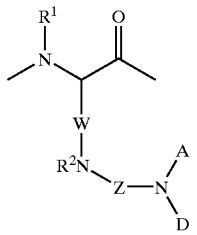

wherein $R^1$ is H, OH, a peptide, a sugar, a targeting molecule, lower alkyl, substituted lower alkyl, or a protecting group that can be removed under the conditions of peptide synthesis; $R^2$ is H, lower alkyl, or substituted lower alkyl; W is from 1–20 atoms long and is selected from the group consisting of cycloalkyl, aryl, or alkaryl groups, a substituted or unsubstituted alkylene chain, and a chain substituted with at least one heteroatom;

Z is an amino acid or a peptide containing 2–5 residues, or Z is $COCH_2$ or $COCH(CH_2SP^2)$, in which $P^2$ is H or a sulfur protecting group;

A and D are the same or different, and each is selected from the group consisting of H, $COCH_2NR^3NR^4C(S)NHR^5$, $COCH_2NR^6NR^7C(S)NHR^8$, $COCH_2NR^9NR^{10}C(O)CH_2SP^2$, $CONR^{11}NR^{12}C(O)CH_2SP^2$, $NR^{13}C(S)NHR^{14}$, or $COCH_2NR^{15}COCH_2SP^2$, $R^3$, $R^4$, $R^6$, $R^7$, $R^9$, $R^{10}$, $R^{11}$, $R^{12}$, $R^{13}$, and $R^{15}$ are the same or different, and each represents H, lower alkyl, or substituted lower alkyl; and $R^5$, $R^8$, and $R^{14}$ are the same or different and each is H, lower alkyl, substituted lower alkyl, aryl, or substituted aryl,

*or $X^5$ is selected from the group consisting of:*

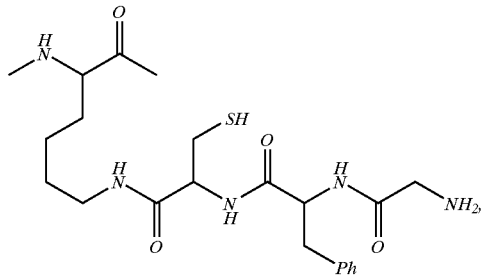

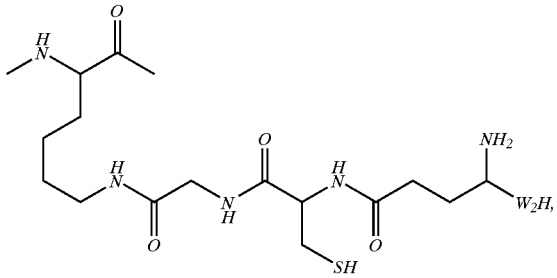

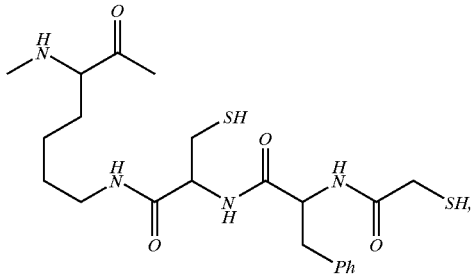

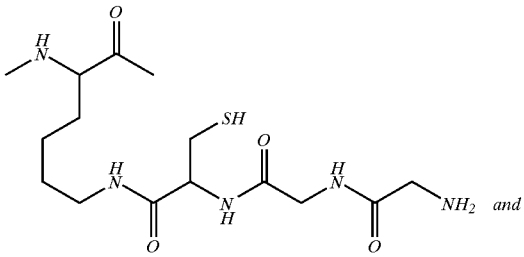

and

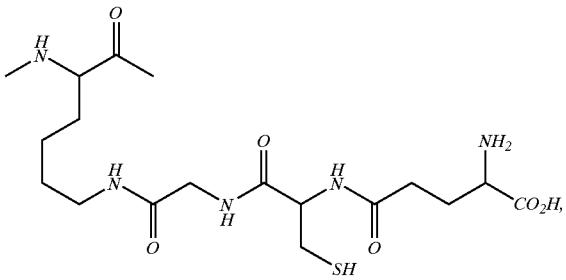

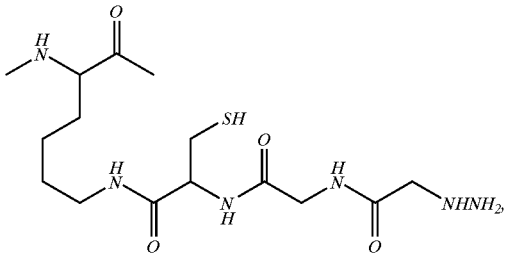

-continued

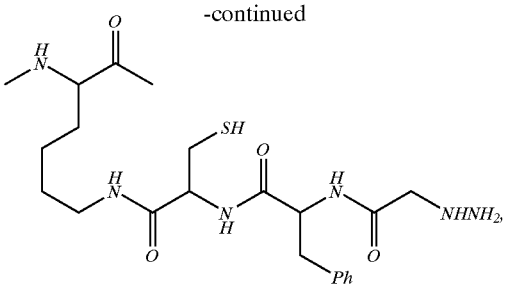

*wherein said amino acid sequence contains at least one thiol or thiocarbonyl group;* and then contacting said solution with $^{99m}$pertechnetate, $^{186}$perrhenate or $^{188}$perrhenate and recovering the radiolabeled peptide.

22. A method of preparing peptides according to claim 1, comprising [the] coupling [of] amino acids and amino acid analogues by solid phase peptide synthesis.

* * * * *